US010238815B2

(12) United States Patent
Imai et al.

(10) Patent No.: US 10,238,815 B2
(45) Date of Patent: Mar. 26, 2019

(54) PUNCTURE ASSISTING DEVICE AND PUNCTURE DEVICE SET

(71) Applicant: TERUMO KABUSHIKI KAISHA, Tokyo (JP)

(72) Inventors: Masaomi Imai, Kanagawa (JP); Ruriko Iibuchi, Kanagawa (JP); Manabu Arinobe, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 161 days.

(21) Appl. No.: 15/223,625

(22) Filed: Jul. 29, 2016

(65) Prior Publication Data
US 2016/0331910 A1    Nov. 17, 2016

Related U.S. Application Data

(63) Continuation of application No. PCT/JP2015/000431, filed on Jan. 30, 2015.

(30) Foreign Application Priority Data

Jan. 31, 2014 (JP) ................................. 2014-017831

(51) Int. Cl.
*A61M 5/42*    (2006.01)
*A61M 5/315*    (2006.01)
(Continued)

(52) U.S. Cl.
CPC ........ *A61M 5/425* (2013.01); *A61M 5/31511* (2013.01); *A61M 5/3287* (2013.01);
(Continued)

(58) Field of Classification Search
CPC ...... A61M 5/425; A61M 5/46; A61M 5/3293; A61M 5/3287
See application file for complete search history.

(56) References Cited

U.S. PATENT DOCUMENTS 3,814,080 A * 6/1974 Norman ................ A61M 5/425
                                                 128/DIG. 26
5,147,306 A * 9/1992 Gubich ................. A61M 5/425
                                                       24/498

(Continued)

FOREIGN PATENT DOCUMENTS

JP        2008-295590 A    12/2008

OTHER PUBLICATIONS

International Search Report dated Apr. 21, 2015 in corresponding application No. PCT/JP2015/000431.
(Continued)

*Primary Examiner* — Bradley J Osinski
(74) *Attorney, Agent, or Firm* — Foley & Lardner LLP

(57) ABSTRACT

A puncture assisting device includes a pair of plate-like pinching portions that face each other, and that are attached to each other so as to be openable and closeable; a biasing portion that biases the pair of pinching portions to be in a closed position; a pair of gripping portions configured to operate the pair of pinching portions to be in an open position; and a rod insertion portion that is disposed between the pair of pinching portions, the rod insertion portion being configured such that a rod portion of a syringe is insertable into the rod insertion portion to widen a gap between the pair of pinching portions.

11 Claims, 18 Drawing Sheets

(51) Int. Cl.
*A61M 5/32* (2006.01)
*A61M 5/46* (2006.01)
(52) U.S. Cl.
CPC ............ *A61M 5/3293* (2013.01); *A61M 5/46* (2013.01); *A61M 2210/083* (2013.01)

(56) References Cited

U.S. PATENT DOCUMENTS

2008/0281269 A1    11/2008  Buysman et al.
2010/0172940 A1*    7/2010  Petrella ................ A61K 31/728
                                                            424/239.1

OTHER PUBLICATIONS

Supplementary European Search Report dated Aug. 30, 2017 in corresponding application No. 15742569.
International Search Report issued in International Patent Application No. PCT/JP2015/000431 dated Apr. 21, 2015.

* cited by examiner

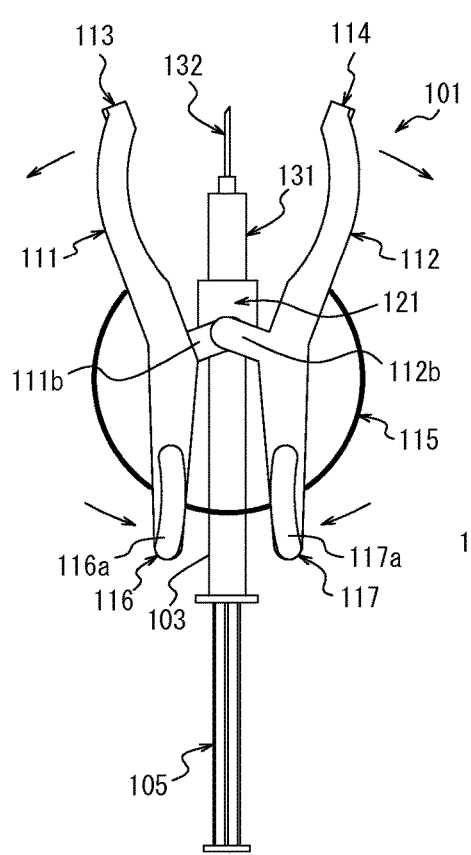
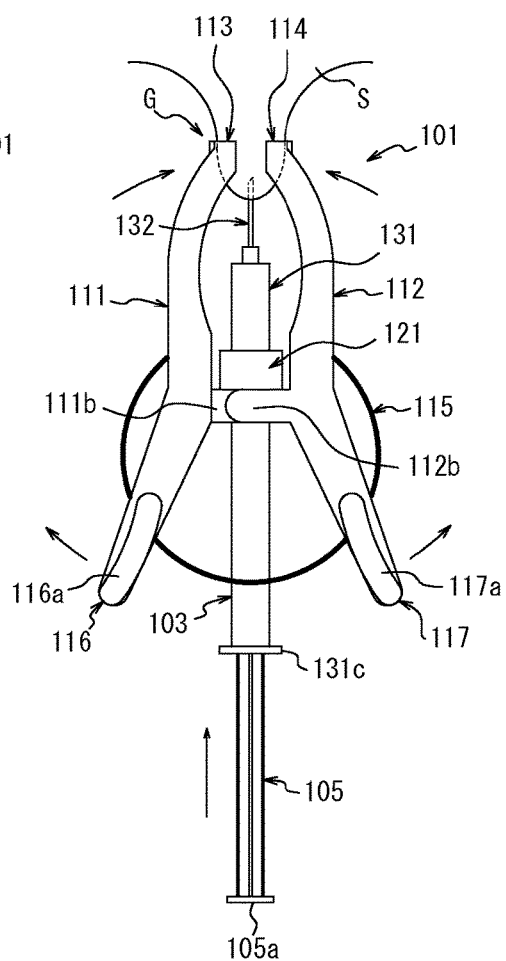

PUNCTURE ASSISTING DEVICE AND PUNCTURE DEVICE SET

CROSS-REFERENCE TO RELATED APPLICATIONS

This application is a continuation of PCT Application No. PCT/JP2015/000431, filed on Jan. 30, 2015, which claims priority to Japanese Patent Application No. 2014-017831, filed on Jan. 31, 2014. These application are hereby incorporated by reference in their entireties.

BACKGROUND

The present disclosure relates to a puncture assisting device and a puncture device set which can be used for subcutaneous injection of a drug.

In the related art, when a drug (drug solution) is subcutaneously injected, a puncture device is used that includes a needle for puncturing the skin so as to intracutaneously or subcutaneously inject the drug through the needle (for example, refer to JP-A-2008-295590).

When the drug is subcutaneously injected by using this puncture device, as an injection site, an upper arm, an abdomen, a thigh, a hip, and the like are mainly selected, since their regions are wide and are located at an easily visible position. The reason is that the drug is easily administered thereto and the skin is likely to be pinched when the needle of the puncture device punctures the skin.

However, in most of these sites, the skin cannot stretch so much. In general, it is known that the upper limit of a drug amount which can be administered is 1 ml. In addition, even if the drug amount to be administered is limited, the administered drug invasively pressurizes a free end of a subcutaneous nerve or causes severe pain due to features of the drug (pH or a surfactant). The subcutaneous injection is basically carried out without anesthesia. In addition, in many cases, the drug has to be continuously injected multiple times. Accordingly, pain relief during the injection has been required.

Therefore, a method has been proposed in which the subcutaneous injection is carried out through the skin of an elbow joint stretching portion at an elbow instead of the above-described sites. The skin of the elbow joint stretching portion at the elbow is more likely to stretch than the skin of other sites, and does not have anatomically major nerves or blood vessels which are present therein. Therefore, a large amount of the drug can be subcutaneously injected without causing pain, compared to other sites.

SUMMARY

In recent years, drugs such as biological products administered by subcutaneous injection have increased. In addition, it has been observed that a large amount of the drug tends to be administered at one time in order to lengthen the duration of drug effects. In addition, it has also been observed that some drugs are subcutaneously injected by oneself (self-administration) in treating rheumatoid arthritis or multiple sclerosis. Therefore, if the drug can be subcutaneously injected into a skin of an elbow joint stretching portion at an elbow by oneself, the subcutaneous injection leads to improved convenience in that the number of times for outpatient treatment or inpatient treatment is reduced.

However, the skin of the elbow joint stretching portion at the elbow is a site which cannot be touched by a hand on the same side. Accordingly, it is necessary to carry out the subcutaneous injection using one hand. Consequently, there are difficulties in subcutaneously injecting the drug into the skin of the elbow joint stretching portion at the elbow by oneself.

Embodiments of the present invention are made in view of the above-described problem, and an object thereof is to provide a puncture assisting device or a puncture assisting device and a puncture device set which enable a drug to be easily and subcutaneously injected into a skin of an elbow joint stretching portion at an elbow by oneself.

A puncture assisting device according to one embodiment of the present invention has a pair of plate-like pinching portions that face each other, and that are attached to each other so as to be openable and closeable, a biasing portion that biases the pair of pinching portions to be in a closed position, a pair of gripping portions that can operate the pair of pinching portions to be in an open position, and a rod insertion portion that is disposed between the pair of pinching portions, and into which a rod portion for widening a gap between the pair of pinching portions is inserted.

In the above-described configuration of the puncture assisting device, the biasing portion may be a U-shaped plate spring including a first plate-like piece supported by one of the pinching portions, a second plate-like piece supported by the other of the pinching portions, and a curved piece for connecting the first plate-like piece and the second plate-like piece to each other, and it is preferable that the rod insertion portion is disposed between the first plate-like piece and the second plate-like piece.

In addition, in the above-described configuration of the puncture assisting device, it is preferable that the rod insertion portion has a portion whose sectional area is smaller than a sectional area of the rod portion.

Furthermore, in the above-described configuration of the puncture assisting device, the rod insertion portion may have a portion whose sectional area gradually decreases toward an inner side from an entrance side, and it is preferable that the gap between the pair of pinching portions is gradually widened as the rod portion is inserted into the rod insertion portion.

Furthermore, in the above-described configuration of the puncture assisting device, it is preferable that a puncture guide portion into which a needle of a syringe is inserted is disposed in a side portion of at least one of the pinching portions.

Furthermore, in the above-described configuration of the puncture assisting device, it is preferable that the puncture guide portion is formed in a ring shape including a guide hole having a smaller diameter than an outer diameter of a needle support portion of the syringe.

The present disclosure relates to the above-described puncture assisting device and a puncture device set. The puncture device set has the above-described puncture assisting device and a syringe in which the rod portion is disposed in a plunger.

In the above-described configuration of the puncture device set, the rod portion may be formed in a shape whose sectional area gradually decreases toward a distal end, and it is preferable that a gap between a pair of pinching portions is gradually widened as the rod portion is inserted into the rod insertion portion.

For example, a drug administration method (drug solution injection method) which can be performed by using the puncture assisting device and the puncture device set according to an embodiment of the present invention is as follows.

The drug administration method includes a skin pinching process of pinching a skin of an elbow joint stretching portion at an elbow by using a skin collecting portion of the puncture assisting device, a syringe setting process of setting a syringe into a syringe insertion portion of the puncture assisting device which nips the skin of the elbow joint stretching portion at the elbow, a puncture process of causing a needle of the syringe to puncture the skin of the elbow joint stretching portion at the elbow which is pinched by the skin collecting portion, a drug injection process of injecting a drug into the skin of the elbow joint stretching portion at the elbow through the needle by pushing a plunger of the syringe, and a needle removal process of removing the needle of the syringe from the skin of the elbow joint stretching portion at the elbow which is pinched by the skin collecting portion.

On the assumption of the above-described configuration, the drug administration method further includes a releasing process of releasing a force of the skin collecting portion which nips the skin of the elbow joint stretching portion at the elbow after the needle removal process.

On the assumption of the above-described configuration, in the drug administration method, the skin collecting portion has a pair of plate-like pinching portions which face each other. In the puncture process, the needle of the syringe punctures the skin from a lateral side of the pinching portion so as to be parallel to the pinching portion between the pair of pinching portions.

On the assumption of the above-described configuration, in the drug administration method, in the skin pinching process, the skin collecting portion nips the skin of the elbow joint stretching portion at the elbow by adopting a posture in which the pair of pinching portions are orthogonal to a longitudinal direction of an arm.

On the assumption of the above-described configuration, in the drug administration method, in the drug injection process, a gap between the pair of pinching portions is gradually widened by inserting a rod portion into a rod insertion portion disposed between the pair of pinching portions.

On the assumption of the above-described configuration, the drug administration method further has a puncture depth regulating process of regulating a depth of the needle of the syringe which punctures the skin.

On the assumption of the above-described configuration, the drug administration method further has a collecting process of collecting the skin of the elbow joint stretching portion at the elbow before the skin pinching process.

According to an embodiment of the present invention, a puncture assisting device stably nips a skin of an elbow joint stretching portion at an elbow, and a needle of a syringe punctures the skin pinched by the puncture assisting device, thereby enabling a drug to be subcutaneously administered. Therefore, subcutaneous injection can be easily and safely carried out by oneself.

BRIEF DESCRIPTION OF THE DRAWINGS

FIG. 4A illustrates a state before the skin is pinched, and FIG. 4B illustrates a state after the skin is pinched.

FIG. 5A illustrates a state where the syringe is set in a puncture guide portion, and FIG. 5B illustrates a state where the needle of the syringe punctures the skin.

FIG. 7A illustrates a state before the rod portion is inserted into the rod insertion portion, and FIG. 7B illustrates a state after the rod portion is inserted into the rod insertion portion.

FIG. 10A illustrates a state before the skin is pinched, and FIG. 10B illustrates a state after the skin is pinched.

FIG. 12A illustrates a state where the syringe is set in a syringe insertion portion, and FIG. 12B illustrates a state where the needle of the syringe punctures the skin.

FIGS. 14A and 14B are views illustrating another procedure of a drug administration method using the puncture assisting device illustrated in FIG. 9. FIG. 14A illustrates a state before the skin is pinched, and FIG. 14B illustrates a state after the skin is pinched.

DETAILED DESCRIPTION

Hereinafter, a first embodiment according to the present invention will be described as an example with reference to FIGS. 1 to 8.

Figure 1:
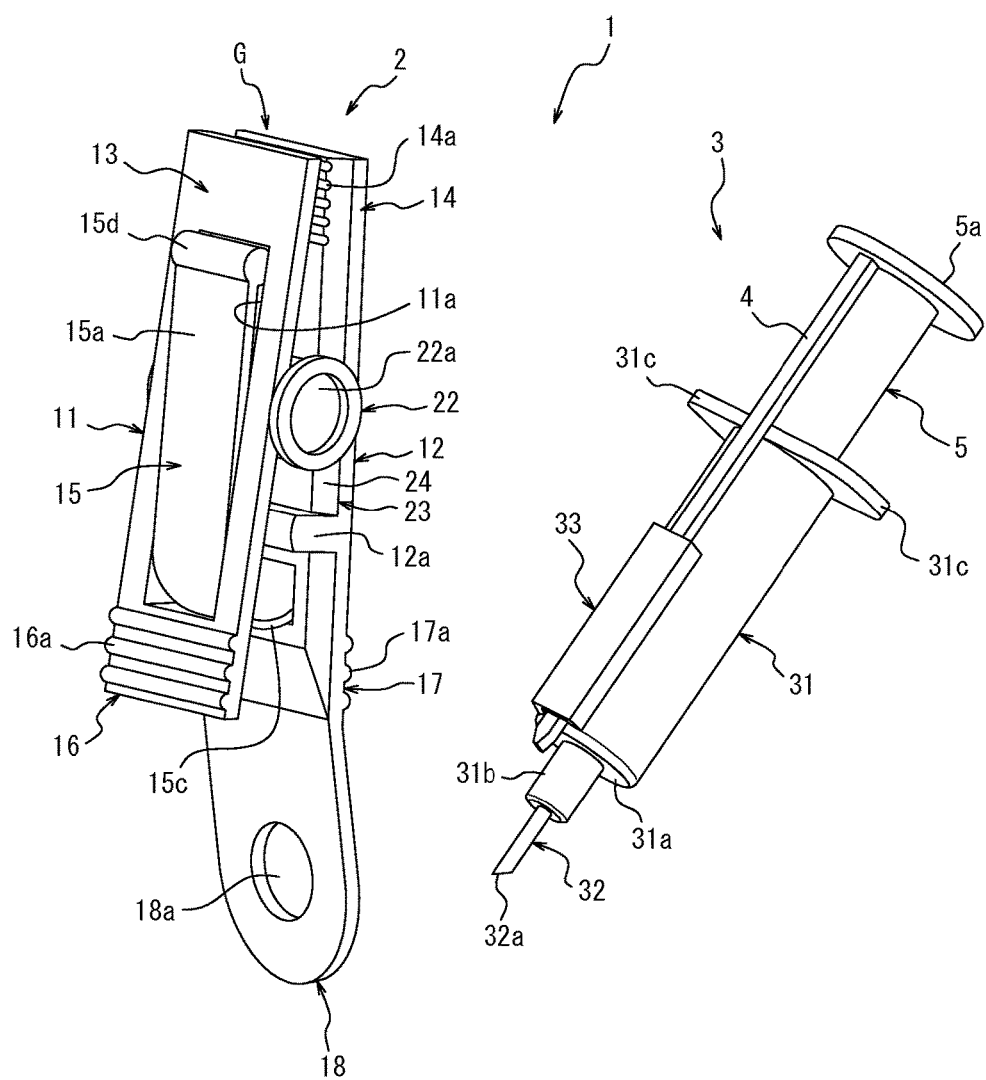
FIG. 1 is a perspective view of a puncture assisting device and a syringe that are included in a puncture device set according to a first embodiment of the present invention.

A puncture device set 1 according to the first embodiment of the present invention which is illustrated in FIG. 1 is used when a drug such as biological products is subcutaneously injected into a skin of an elbow joint stretching portion at an elbow in various treatments for rheumatoid arthritis or multiple sclerosis, for example. The puncture device set 1 has a puncture assisting device 2 and a syringe 3. The syringe 3 includes a plunger 5 having a plunger side rod portion 4 corresponding to the puncture assisting device 2 disposed thereon.

As illustrated in FIGS. 1 and 2, the puncture assisting device 2 includes a first pinching piece 11 and a second pinching piece 12. The first pinching piece 11 and the second pinching piece 12 are each configured as a rectangular plate body, and are attached to each other in a thickness direction, in an arrangement where outer shapes thereof are substantially aligned with each other. A projection piece portion 12a which extends straight in a width direction thereof and which protrudes toward an inner side surface (surface facing the second pinching piece 12 side) of the first pinching piece 11 is integrally disposed in an intermediate portion in the longitudinal direction of an inner side surface (surface facing the first pinching piece 11 side) of the second pinching piece 12. The inner side surface of the first pinching piece 11 is in contact with an upper surface of the projection piece portion 12a. The upper surface of the projection piece portion 12a is curved in an arc shape when viewed from a lateral side of the pinching pieces 11 and 12. The first pinching piece 11 can pivot relative to the second pinching piece 12 by using the upper surface of the projection piece portion 12a as a fulcrum.

For example, the first pinching piece 11 and the second pinching piece 12 can be made of a synthetic resin such as an acrylic resin or an ABS resin, but can also be formed of other materials such as metal made of stainless steel and an aluminum alloy.

In addition, without being limited to a configuration in which the first pinching piece 11 and the second pinching piece 12 are supported by the above-described projection piece portion 12a and are attached to each other so as to be relatively pivotable, it is also possible to adopt a configuration in which the first pinching piece 11 and the second pinching piece 12 are attached to each other so as to be relatively pivotable by using other pivoting mechanisms such as a hinge (joint), for example.

A portion of the first pinching piece 11 on a distal side (upper side in FIGS. 1 and 2) further from the portion in contact with the projection piece portion 12a is a plate-like first pinching portion 13. A portion of the second pinching piece 12 on the distal side further from the projection piece portion 12a is a plate-like second pinching portion 14 which faces the first pinching portion 13. The pair of these pinching portions 13 and 14 can be opened and closed so as to move close to or away from each other by relatively pivoting the first pinching piece 11 and the second pinching piece 12. Then, the first pinching portion 13 and the second pinching portion 14 which are opened and closed can pinch the skin by being closed in a state where the skin of the elbow joint stretching portion at the elbow is pinched therebetween. In addition, the skin pinched therebetween can be released by opening the first pinching portion 13 and the second pinching portion 14. The respective inner side surfaces of the pinching portions 13 and 14 can have a configuration for preventing the pinched skin from slipping out, for example, such as four grooves 13a and 14a extending in the illustrated width direction. The first pinching portion 13 and the second pinching portion 14 configure a skin collecting portion G.

A plate spring 15 functioning as a biasing portion is mounted on the puncture assisting device 2. The first pinching portion 13 and the second pinching portion 14 are biased by the plate spring 15 to be in a closed position, that is, in a direction of moving close to each other, thereby being brought into contact with each other in a natural state. The first pinching portion 13 and the second pinching portion 14 can also adopt a configuration of moving away from each other by leaving a regulated gap therebetween in a natural state.

Figure 2A:
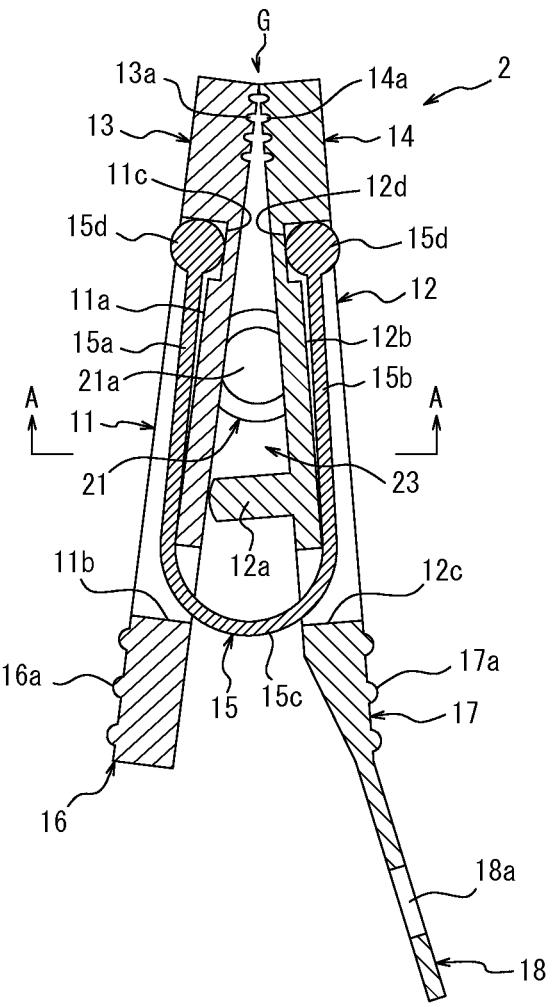
FIG. 2A is a longitudinal sectional view of the puncture assisting device illustrated in FIG. 1.
Figure 2B:
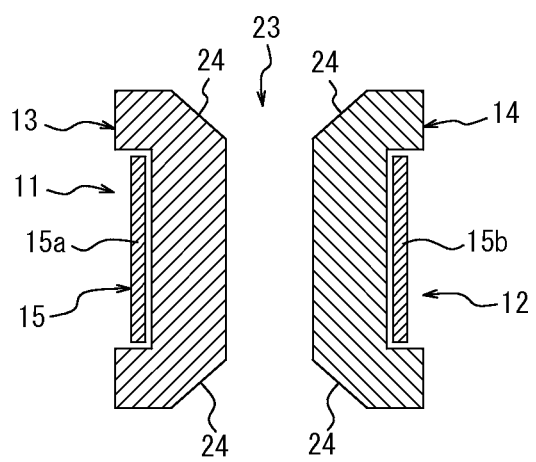
FIG. 2B is a sectional view taken along line A-A in FIG. 2A.

More specifically, as illustrated in FIGS. 2A and 2B, the plate spring 15 is formed in a U-shape in which a first plate-like piece 15a and a second plate-like piece 15b are connected to each other by a curved piece 15c. Concave portions 11a and 12b extending along the longitudinal direction are respectively disposed on an outer side surface of the first pinching piece 11 and the second pinching piece 12. The first plate-like piece 15a of the plate spring 15 is arranged in the concave portion 11a disposed in the first pinching piece 11, and is supported by the first pinching portion 13. The second plate-like piece 15b of the plate spring 15 is arranged in the concave portion 12b disposed in the second pinching piece 12, and is supported by the second pinching portion 14. Through-holes 11b and 12c respectively penetrating the pinching pieces 11 and 12 in the thickness direction are disposed on a proximal side of the respective concave portions 11a and 12b. The curved piece 15c of the plate spring 15 connects the first plate-like piece 15a and the second plate-like piece 15b to each other via the through-holes 11b and 12c. In addition, columnar locking portions 15d are respectively and integrally disposed in a distal end of the first plate-like piece 15a and the second plate-like piece 15b. The locking portions 15d engage with locking grooves 11c and 12d respectively disposed on a bottom of the concave portions 11a and 12b, thereby preventing from being separated from the first pinching piece 11 and the second pinching piece 12 of the plate spring 15 and holding a combined state between the first pinching piece 11 and the second pinching piece 12.

For example, as the plate spring 15, a metal-made plate spring formed using a steel plate made of spring steel or stainless steel can be used, but for example, a resin-made plate spring can also be used. In addition, the biasing portion is not limited to the plate spring 15 having the above-described configuration. For example, other configurations using a helical spring, a torsion spring, and an elastic material such as rubber can also be adopted as long as the first pinching portion 13 and the second pinching portion 14 can be biased to be in a closed position.

A portion of the first pinching piece 11 which is located on the proximal side (opposite side to a side having the first pinching portion 13) further from the portion coming into contact with the projection piece portion 12a is a first gripping portion 16. A portion of the second pinching piece 12 which is located on the proximal side (opposite side to a side having the second pinching portion 14) further from the projection piece portion 12a is a second gripping portion 17. In a state where the first pinching portion 13 and the second pinching portion 14 are closed, the first gripping portion 16 and the second gripping portion 17 face each other by leaving a gap therebetween. For example, these gripping portions 16 and 17 are gripped and pinched by two fingers, and are operated in the direction of moving close to each other. In this manner, the pair of pinching portions 13 and 14 can be opened by relatively pivoting the first pinching piece 11 and the second pinching piece 12. If the operation of the gripping portions 16 and 17 is halted, a spring force of the plate spring 15 causes the pair of pinching portions 13 and 14 to return to a closed state. That is, the pair of pinching portions 13 and 14 can be opened and closed by operating these gripping portions 16 and 17. For example, as illustrated, a configuration for preventing slip such as three ribs 16a and 17a extending in the width direction can be disposed on the outer side surface of the respective gripping portions 16 and 17.

According to the configuration of the puncture assisting device 2 having a clip shape in this way, the gripping portions 16 and 17 are pinched and pinched by two fingers so as to open the pair of pinching portions 13 and 14. In this state, the pair of pinching portions 13 and 14 are pushed against the skin of the elbow joint stretching portion at the elbow in the vertical direction. Next, the operation of the gripping portions 16 and 17 is restarted. In this manner, the skin can be pinched and held between the pair of pinching portions 13 and 14.

A holding piece 18 extending in the longitudinal direction is integrally disposed on a proximal end of the second pinching piece 12. The holding piece 18 is formed in a plate-like shape which is thinner than that of the second pinching piece 12, and is slightly inclined toward the outer side surface of the second pinching piece 12. In a state where the skin is pinched between the pair of pinching portions 13 and 14, the holding piece 18 is pulled, thereby enabling tension to be applied to the skin pinched by the pinching portions 13 and 14. For example, the holding piece 18 can adopt a configuration for preventing slip, such as a circular hole 18a and a rib as illustrated.

A first puncture guide portion (syringe insertion portion) 21 is disposed in a side portion of the first pinching portion 13. A second puncture guide portion (syringe insertion portion) 22 is disposed in a side portion of the second pinching portion 14. The puncture guide portions 21 and 22 are respectively formed in a ring shape including circular guide holes 21a and 22a. The syringe 3 can be inserted into the guide holes 21a and 22a. The guide hole 21a of the first puncture guide portion 21 adopts a posture facing between the first pinching portion 13 and the second pinching portion 14, and is integrally disposed in the side portion of the first pinching portion 13. The guide hole 22a of the second puncture guide portion 22 adopts a posture facing between the first pinching portion 13 and the second pinching portion 14, and is integrally disposed in the side portion of the second pinching portion 14. Axial centers of the guide holes 21a and 22a of the two puncture guide portions 21 and 22 are coincident with each other, when the pair of pinching portions 13 and 14 are closed so as to come into contact with each other.

A rod insertion portion 23 is disposed between the first pinching portion 13 and the second pinching portion 14. In the present embodiment, the rod insertion portion 23 is disposed between the first plate-like piece 15a and the second plate-like piece 15b of the plate spring 15, which is a region pinched between the projection piece portion 12a and the puncture guide portions 21 and 22, between the first pinching portion 13 and the second pinching portion 14, and is open toward a side of the first pinching portion 13 and the second pinching portion 14. As illustrated in FIG. 2B, a portion between the inner side surface and the side surface of the first pinching piece 11 and a portion between the inner side surface and the side surface of the second pinching piece 12 are respectively chamfered slopes 24. In this manner, in the rod insertion portion 23, a sectional area in an entrance (opening end) thereof is larger than a sectional area of the plunger side rod portion 4 disposed in the plunger 5 of the syringe 3. The sectional area gradually decreases from the entrance side toward the inner portion side. The central portion is formed in a shape having a fixed sectional area which is smaller than the sectional area of the plunger side rod portion 4. In addition, in a state where the first pinching portion 13 and the second pinching portion 14 are closed, a gap between the inner side surface of the first pinching portion 13 and the inner side surface of the second pinching portion 14 in the central portion having the fixed sectional area of the rod insertion portion 23 has a width dimension which is smaller than that of the plunger side rod portion 4 to be inserted into the rod insertion portion 23. Therefore, if the plunger side rod portion 4 is inserted into the rod insertion portion 23, in response to the insertion, a gap between the pair of pinching portions 13 and 14 is gradually widened by the plunger side rod portion 4.

As illustrated in FIG. 1, the syringe 3 includes an outer cylinder body 31 and a needle 32 in addition to the plunger side rod portion 4 and the plunger 5 which function as the above-described rod portion.

The outer cylinder body 31 is formed in a cylindrical shape in which one end is opened and the other end is closed by a needle support portion 31a, and internally has an accommodation chamber for accommodating a drug. The plunger 5 is formed in a columnar shape having the diameter corresponding to the inner diameter of the outer cylinder body 31, is inserted into the outer cylinder body 31 from the opening end of the outer cylinder body 31, and is mounted on the outer cylinder body 31 so as to be relatively movable in the axial direction. For example, the outer cylinder body 31 or the plunger 5 can be made of a resin or glass. In addition, the plunger 5 can also adopt a configuration in which a sealing member formed of an elastic body such as rubber and sealing a portion between the plunger 5 and an inner peripheral surface of the outer cylinder body 31 is mounted on the distal end of the plunger 5.

A cylindrical hub 31b having a smaller diameter than a needle support portion 31a is integrally disposed in the axial center of the needle support portion 31a, and the needle 32 is fixed to the hub 31b. The needle 32 is a hollow needle, and a needle tip 32a thereof is obliquely cut, and is formed so as to have an acute angle. In addition, a proximal portion of the needle 32 is fixed to the hub 31b, and a lumen thereof communicates with the inside of the outer cylinder body 31 via the hub 31b. As the needle 32, for example, those which are formed of a metal material such as stainless steel, an aluminum alloy, a titanium alloy, and the like can be used.

The outer diameter of the needle support portion 31a of the syringe 3, that is, the outer diameter of the outer cylinder body 31 is larger than the inner diameter of the guide holes 21a and 22a of the puncture guide portions 21 and 22. The outer diameter of the hub 31b of the syringe 3 is smaller than the inner diameter of the guide holes 21a and 22a of the puncture guide portions 21 and 22. Therefore, the needle 32 and the hub 31b of the syringe 3 can be inserted into the guide holes 21a and 22a of the puncture guide portions 21 and 22 from a lateral side of the puncture assisting device 2. In addition, the needle support portion 31a comes into contact with the puncture guide portions 21 and 22. In this manner, it is possible to regulate an insertion depth, when the needle 32 and the hub 31b are inserted into the puncture guide portions 21 and 22, that is, into the inside of the pair of pinching portions 13 and 14.

A pair of finger hook flanges 31c extending outward in a radial direction thereof is symmetrically arranged, and is integrally disposed in the opening end of the outer cylinder body 31. On the other hand, a disc-shaped thrusting flange 5a is integrally disposed in the proximal end of the plunger 5. In this manner, a forefinger and a middle finger are hooked into the pair of finger hook flanges 31c of the outer cylinder body 31, and a thumb is hooked into the thrusting flange 5a of the plunger 5. The thumb pushes the plunger 5 toward the inside of the outer cylinder body 31. In this manner, it is possible to easily perform an operation for dispensing a drug accommodated inside the outer cylinder body 31 outward from the needle tip 32a of the needle 32.

Figure 3:
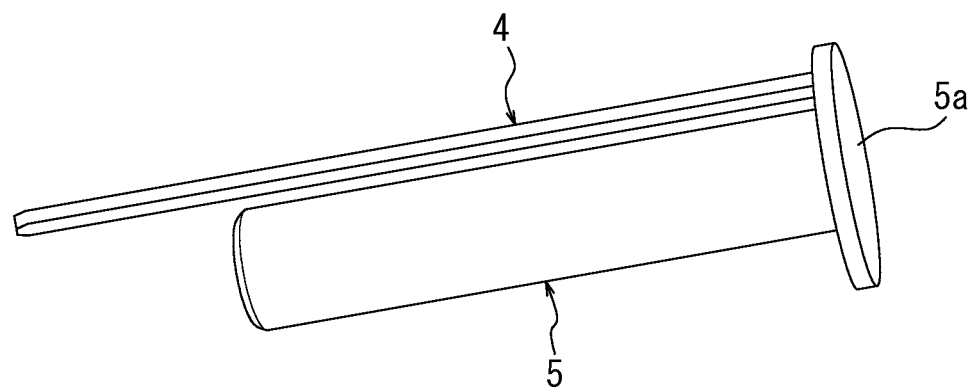
FIG. 3 is a perspective view of a plunger of the syringe illustrated in FIG. 1.

As illustrated in FIG. 3, the plunger side rod portion 4 is disposed in the plunger 5. More specifically, the plunger side rod portion 4 is formed in a rod shape which is longer than the plunger 5 and which has a rectangular cross section, and a proximal end thereof is integrally connected to a lower surface of the thrusting flange 5a of the plunger 5. In addition, the plunger side rod portion 4 is arranged on the outside in the radial direction of the plunger 5 by leaving a gap from the plunger 5, and is arranged parallel to the plunger 5 so as to extend along the axial direction of the plunger 5. A distal end of the plunger side rod portion 4 can employ an acute angular shape by means of chamfering.

As in the present embodiment, in a case where the plunger side rod portion 4 is integrally disposed in the plunger 5, it is preferable to form both of these through injection molding by using a resin material. Without being limited to a configuration of being integrally disposed in the plunger 5, for example, the plunger side rod portion 4 may also adopt a configuration of being fixed to the plunger 5 by using a fastening member, an adhesive, or the like, or by means of fitting and the like.

In addition, the rod portion is not limited to the plunger side rod portion 4 disposed integrally with the plunger 5 of the syringe 3, and can also adopt a configuration in which the rod portion is independently disposed separate from the plunger 5. In this case, the rod portion can be independently operated separate from the plunger 5.

A tunnel-shaped rod support portion 33 extending in the axial direction from a portion of the needle support portion 31a is integrally disposed at a position where the outer peripheral surface of the outer cylinder body 31 is shifted from the pair of finger hook flanges 31c as much as an angle of 90 degrees. The plunger side rod portion 4 is inserted into the inside of the rod support portion 33. An inner surface of the rod support portion 33 comes into sliding contact with an outer surface of the plunger side rod portion 4, thereby supporting the plunger side rod portion 4 so as to be slidable.

According to this configuration, if the plunger 5 is pushed to the inside of the outer cylinder body 31, that is, toward the needle 32 side, in order to dispense a drug outward from the needle tip 32a of the needle 32, the plunger side rod portion 4 gradually protrudes parallel to the needle 32 from the distal side of the outer cylinder body 31, in response to the pushed plunger 5.

Next, referring to FIGS. 4 to 7, a procedure will be described in a drug administration method (drug solution injection method) in which a drug is subcutaneously injected into a skin S of an elbow joint stretching portion at an elbow by using the puncture device set 1 according to the first embodiment of the present invention.

Figure 4A:
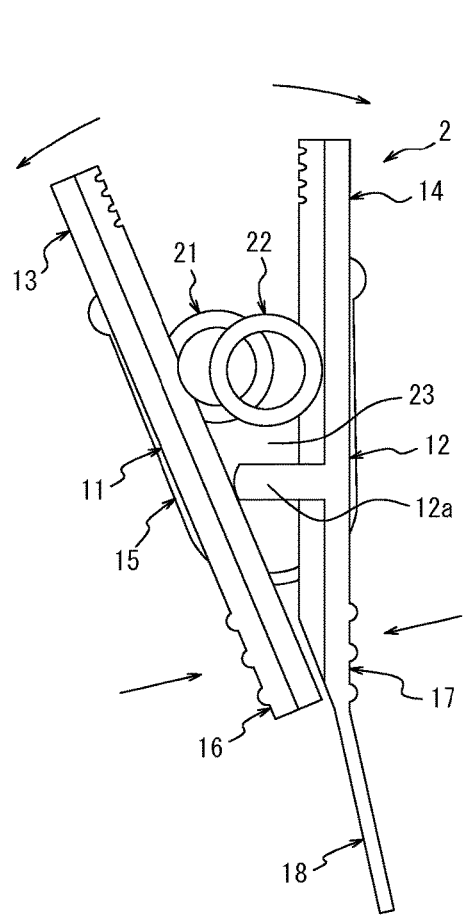
FIGS. 4A and 4B are views illustrating a procedure in which the puncture assisting device illustrated in FIG. 1 nips a skin of an elbow joint stretching portion at an elbow.

First, a skin pinching process of pinching the skin S of the elbow joint stretching portion at the elbow is performed by using the pair of pinching portions 13 and 14 of the puncture assisting device 2, that is, the skin collecting portion G. As illustrated in FIG. 4A, in the skin pinching process, a pair of gripping portions 16 and 17 are pinched and pinched by two fingers, for example, so as to open the pair of pinching portions 13 and 14. The inner side surface of the second gripping portion 17 is cut out so as to be gradually thinner toward the holding piece 18. When the pair of pinching portions 13 and 14 are opened, an opening degree of the pair of pinching portions 13 and 14 can be increased by causing the first gripping portion 16 to reach the cutout portion of the inner side surface.

Figure 4B:
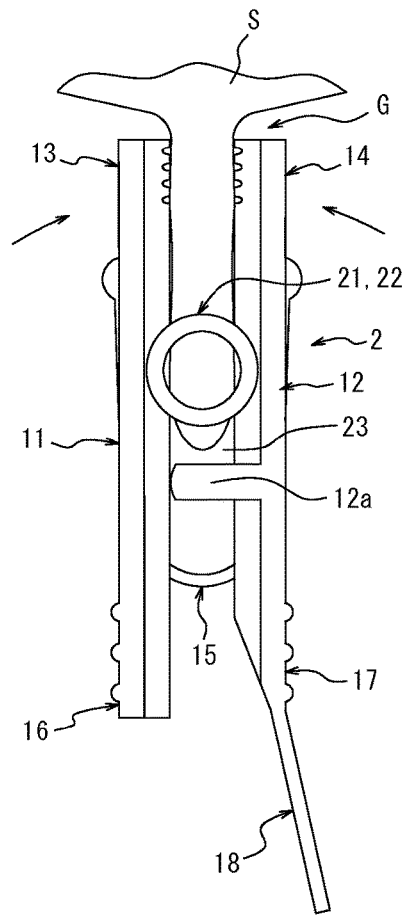

Next, in this state, the pair of pinching portions 13 and 14 are pushed against the skin S of the elbow joint stretching portion at the elbow in the vertical direction so as to release an operation force applied to the gripping portions 16 and 17. As illustrated in FIG. 4B, the skin S is pinched and held between the pinching portions 13 and 14. At this time, the pinched skin S reaches a site where the puncture guide portions 21 and 22 are disposed between the pair of pinching portions 13 and 14. A spring force is applied to the pair of pinching portions 13 and 14 from the plate spring 15 in the direction for closing both of these. Accordingly, the skin S pinched by the pinching portions 13 and 14 is brought into a state of being pressurized between the pinching portions 13 and 14.

In the skin pinching process, it is preferable to pinch the skin S by adopting a posture in which the pair of pinching portions 13 and 14 are orthogonal to the longitudinal direction of a subcutaneous injection target arm in a state where the arm is stretched, that is, a posture in which the pair of pinching portions 13 and 14 are parallel to each other along the longitudinal direction of the arm. The puncture assisting device 2 nips the skin S by adopting this posture. In this manner, at least any one of the puncture guide portions 21 and 22 can be set in the puncture guide portions 21 and 22 of the syringe 3 so as to face a side of the stretched arm, and the syringe 3 can easily puncture the skin S (to be described later).

In order to pinch the skin S as much as possible between the pair of pinching portions 13 and 14, before the skin pinching process, a collecting process can also be performed in which the skin S of the elbow joint stretching portion at the elbow is collected so as to have a shape for easier pinching. For example, through the same work as that in the skin pinching process, the collecting process can be performed by using a method of pinching the skin S in a wider range, after the skin S is pinched between the pair of pinching portions 13 and 14, the skin S is once detached therefrom, and the pinching portions 13 and 14 are reopened. In this case, a configuration can also be adopted in which the skin S is more likely to be collected by disposing an adhesive material or an uneven shape, for example, in each distal portion of the pair of pinching portions 13 and 14.

Without being limited to the above-described method, the collecting process can be performed by using a method in which the skin S is collected by a hand without using the puncture assisting device 2, or in which the skin S is collected by using other devices.

After the skin S is pinched by the pair of pinching portions 13 and 14, the holding piece 18 is pulled, if necessary. In this manner, tension can be applied to the skin S pinched by the pinching portions 13 and 14.

Figure 5A:
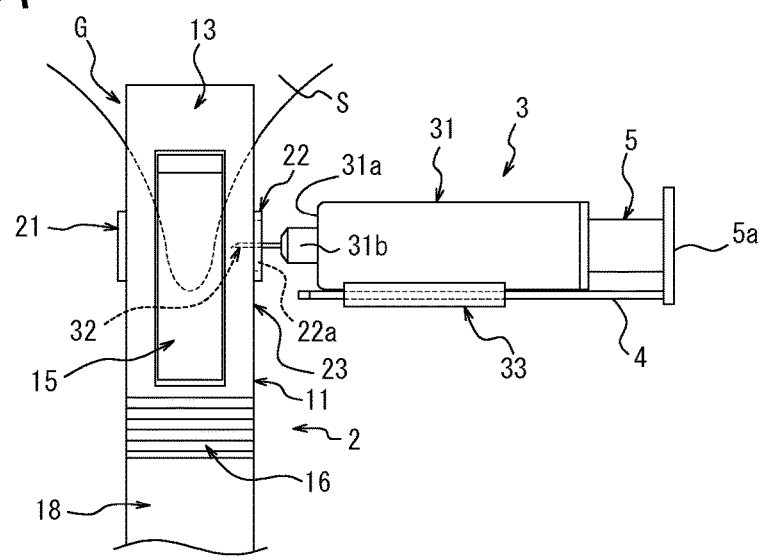
FIGS. 5A and 5B are views illustrating a procedure in which a needle of the syringe punctures the skin pinched by the puncture assisting device.

If the skin S is pinched by the puncture assisting device 2, next, as a syringe setting process, the syringe 3 is set in any one of the puncture guide portions 21 and 22. In the present embodiment, as illustrated in FIG. 5A, in the syringe setting process, the needle 32 of the syringe 3 is inserted into the guide hole 22a of the puncture guide portion 22 from a lateral side of the puncture assisting device 2. In this manner, the syringe 3 is set in the puncture guide portion 22. At this time, the syringe 3 adopts a posture in which the distal end of the plunger side rod portion 4 faces the opening end of the rod insertion portion 23. In this way, the syringe 3 is set in the puncture guide portions 21 and 22. Accordingly, the syringe 3 can be easily and accurately set in the puncture assisting device 2.

Figure 5B:
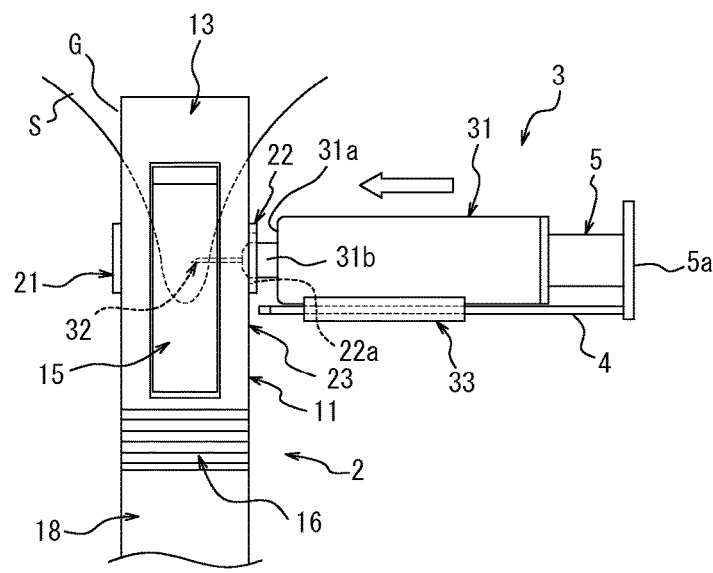

Next, as illustrated in FIG. 5B, as a puncture process, the syringe 3 set in the puncture guide portion 22 is pushed toward a portion between the pair of pinching portions 13 and 14, that is, toward the skin S pinched by the pinching portions 13 and 14 so that the needle 32 of the syringe 3 punctures the skin S. Therefore, the needle 32 punctures the skin S in parallel to the pinching portions 13 and 14 between the pair of pinching portions 13 and 14 and from a lateral side of the pinching portions 13 and 14, that is, from a lateral side of the skin S pinched by the pinching portions 13 and 14.

At this time, the inner diameter of the guide hole 22a of the puncture guide portion 22 is smaller than the outer diameter of the needle support portion 31a of the syringe 3. Accordingly, an insertion amount obtained by the syringe 3 inserted into the puncture guide portion 22 is regulated within a predetermined range in such a way that the needle support portion 31a comes into contact with the puncture guide portion 22. This regulates a puncture depth when the needle 32 punctures the skin S (puncture depth regulating process). Therefore, it is possible to prevent the needle 32 from excessively puncturing the skin S or penetrating the skin S after the syringe 3 is inadvertently and deeply inserted into the puncture guide portion 22.

Figure 6:
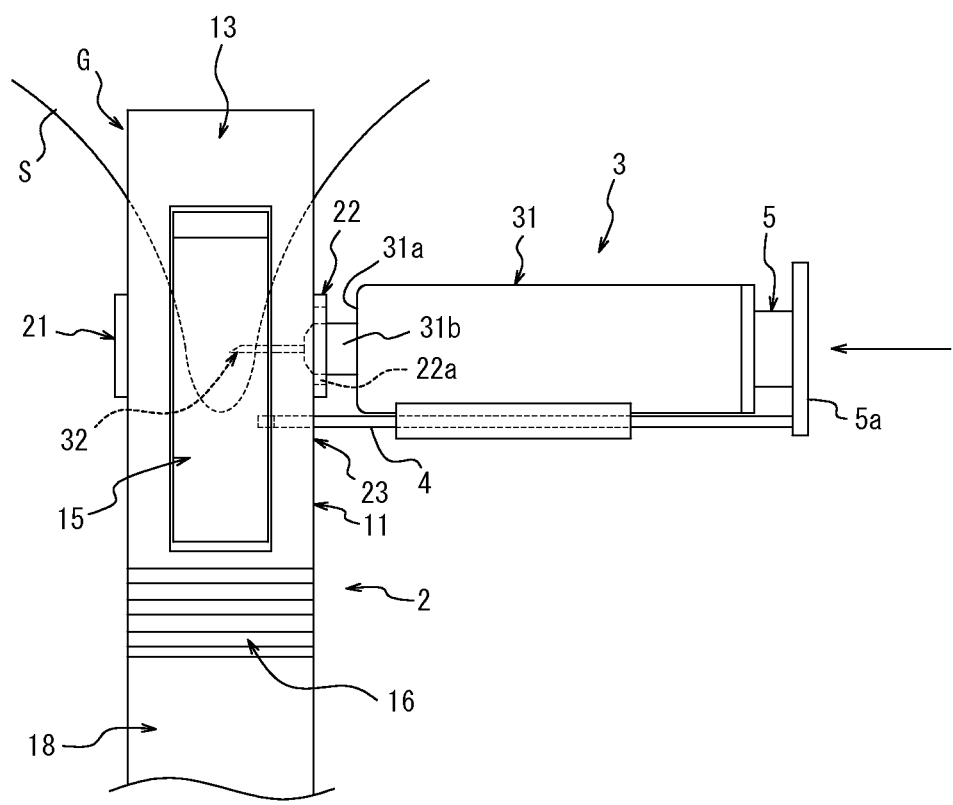
FIG. 6 is a view illustrating a state where a drug solution is injected into the skin by pushing the plunger of the syringe.

If the needle 32 of the syringe 3 punctures the skin S, next, as a drug injection process, as illustrated in FIG. 6, the plunger 5 of the syringe 3 is pushed toward the needle 32 side so as to inject the drug into the inside of the skin S through the needle 32 of the syringe 3.

Figure 7A:
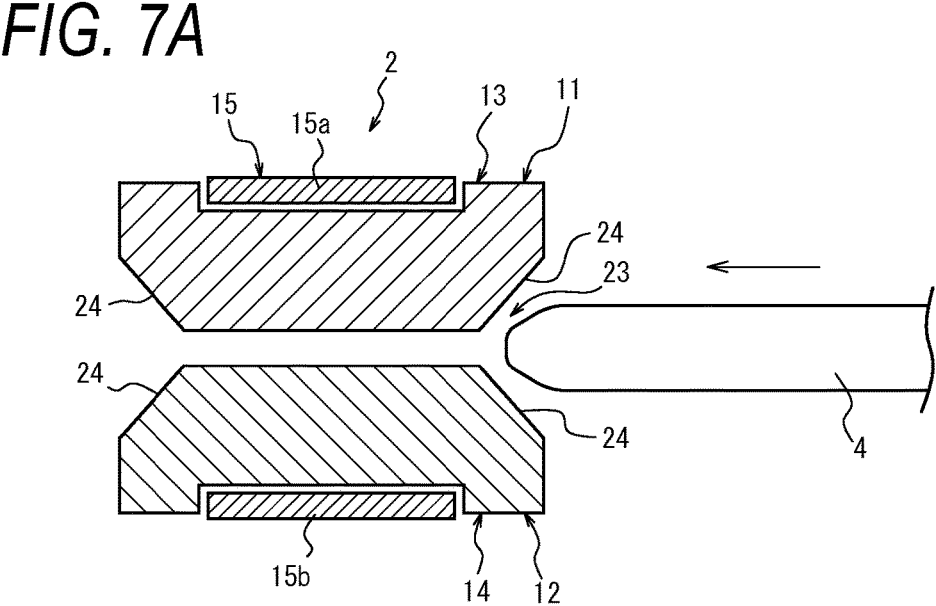
FIGS. 7A and 7B are sectional views illustrating a state where a rod portion is inserted into a rod insertion portion and a pair of pinching portions are pushed to open.
Figure 7B:
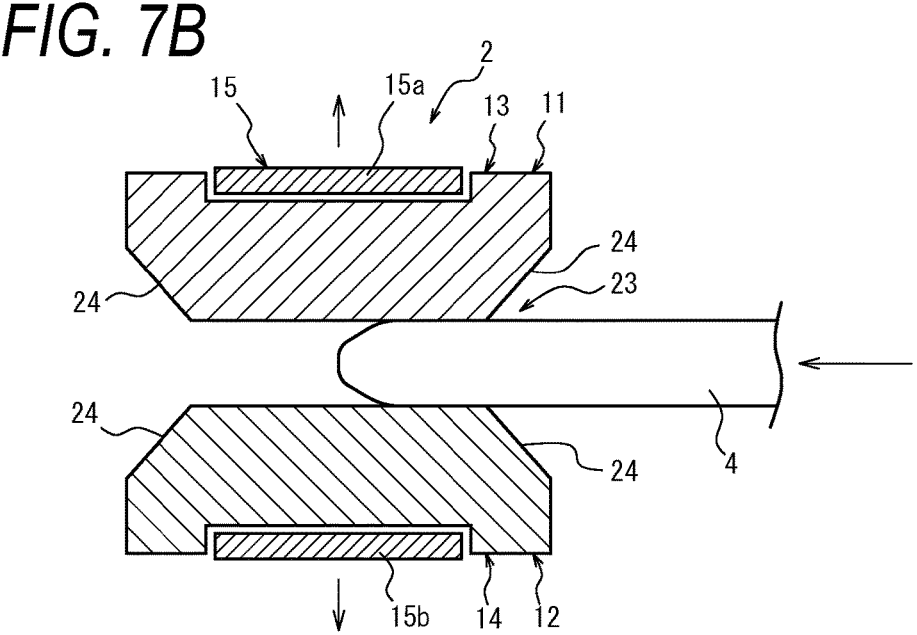

If the plunger 5 is pushed toward the needle 32 side in the drug injection process, the plunger 5 and the plunger side rod portion 4 protrude from the rod support portion 33, and are inserted into the rod insertion portion 23. As illustrated in FIG. 7A, a height dimension of the plunger side rod portion 4 in the illustrated vertical direction is larger than that of a vertical gap between the inner side surfaces of the pair of pinching portions 13 and 14 in a state where the skin S is pinched. Then, if the plunger side rod portion 4 is inserted into the rod insertion portion 23, the plunger side rod portion 4 comes into contact with the slope 24 of the respective pinching portions 13 and 14. As the plunger side rod portion 4 is inserted into the rod insertion portion 23, a gap between the pair of pinching portions 13 and 14 is gradually widened by the plunger side rod portion 4. Then, as illustrated in FIG. 7B, if the plunger side rod portion 4 reaches the intermediate portion of the rod insertion portion 23 and is brought into a state of being pinched between the inner side surfaces of the respective pinching portions 13 and 14, a gap between the pair of pinching portions 13 and 14 pinching the skin S, that is, an opening degree of the pinching portions 13 and 14 becomes constant.

According to this configuration, while the drug is injected into the skin S stably pinched between the pair of pinching portions 13 and 14 of the puncture assisting device 2 through the needle 32 of the syringe 3, the pinching portions 13 and 14 pinching the skin S can be gradually opened. Therefore, the pressure generated in the skin S which is pinched by the pinching portions 13 and 14 is gradually released as the drug is injected. Invasion of the drug due to a pressurized free end of a subcutaneous nerve is reduced. In this manner, a large amount of the drug can be subcutaneously administered.

Figure 8:
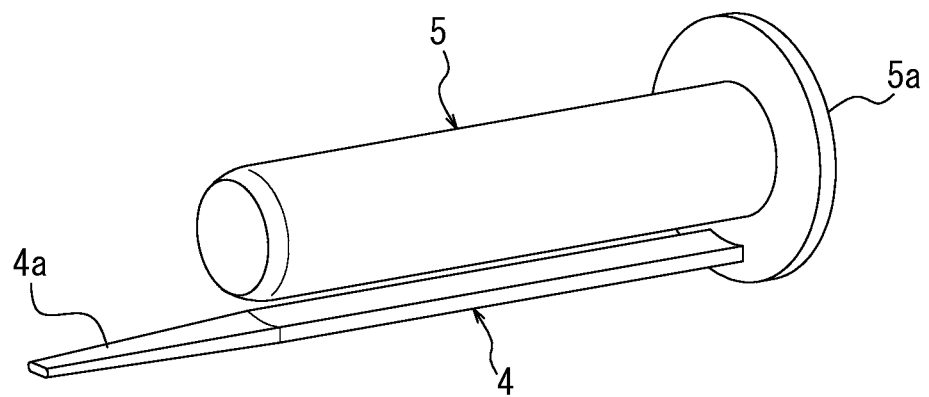
FIG. 8 is a perspective view illustrating a modification example of the rod portion illustrated in FIG. 3.

As illustrated in FIG. 8, the plunger side rod portion 4 can also adopt a configuration in which a tapered distal portion 4a is disposed in the distal end of the plunger side rod portion 4. The tapered distal portion 4a has a shape whose sectional area gradually decreases toward the distal side. In this case, without disposing the slope 24 in the pair of pinching portions 13 and 14, the plunger side rod portion 4 is inserted into the rod insertion portion 23 in the tapered distal portion 4a. In this manner, a gap between the pair of pinching portions 13 and 14 can be gradually widened. The plunger side rod portion 4 having the tapered distal portion 4a disposed therein can also be applied to the configuration in which the slope 24 is disposed in the pair of pinching portions 13 and 14. A tapered angle of the tapered distal portion 4a is adjusted. In this manner, the gap between the pair of pinching portions 13 and 14 can be gradually widened at the timing and to an extent which is suitable for the injection amount of the drug.

If the drug is completely injected into the inside of the skin S by pushing the plunger 5 to reach a regulated position, the syringe 3 is pulled out from the puncture guide portion 22, thereby performing a needle removal process of removing the needle 32 of the syringe 3 from the skin S.

Then, after the needle removal process, a pair of gripping portions 16 and 17 are pinched and pinched by two fingers, thereby performing a releasing process of releasing the force of the pair of pinching portions 13 and 14 pinching the skin S. In the present embodiment, when the drug is injected into the skin S stably pinched between the pair of pinching portions 13 and 14 of the puncture assisting device 2 through the needle 32 of the syringe 3, the plunger side rod portion 4 gradually weakens the pinching force of the pinching portions 13 and 14 pinching the skin S. Accordingly, it is possible to omit the releasing process of releasing the force of the pair of pinching portions 13 and 14 pinching the skin S. In this manner, the skin S into which the drug is injected by the syringe 3 is released from a state of being pinched by the pinching portions 13 and 14 of the puncture assisting device 2, and the drug is completely administered.

In this way, according to the above-described first embodiment of the present invention, the skin S of the elbow joint stretching portion at the elbow is stably pinched by the puncture assisting device 2, and the needle 32 of the syringe 3 punctures the skin S pinched by the puncture assisting device 2 from a lateral side. In this manner, the drug can be administered into the skin S. Therefore, the puncture assisting device 2 is operated by using one hand so as to pinch the skin S of the elbow joint stretching portion at the elbow in the other arm. Subsequently, the syringe 3 is held by using one hand detached from the puncture assisting device 2. The puncture guide portions 21 and 22 are used as a guide, and the needle 32 of the syringe 3 punctures the skin S pinched by the puncture assisting device 2 from a lateral side of the puncture assisting device 2. In this manner, the drug can be easily, safely, and subcutaneously injected into the skin S of the elbow joint stretching portion at the elbow by oneself.

In addition, it is possible to subcutaneously inject the drug into the skin S of the elbow joint stretching portion at the elbow by oneself. Accordingly, compared to a case where the drug is subcutaneously injected into other sites, a large amount of the drug can be administered without causing pain. In addition, a major nerve is not present in the skin S of the elbow joint stretching portion at the elbow. Accordingly, the needle 32 of the syringe 3 can safely puncture the skin S without giving damage to a nerve.

Next, a second embodiment according to the present invention will be described as an example with reference to FIGS. 9 to 16.

Figure 9:
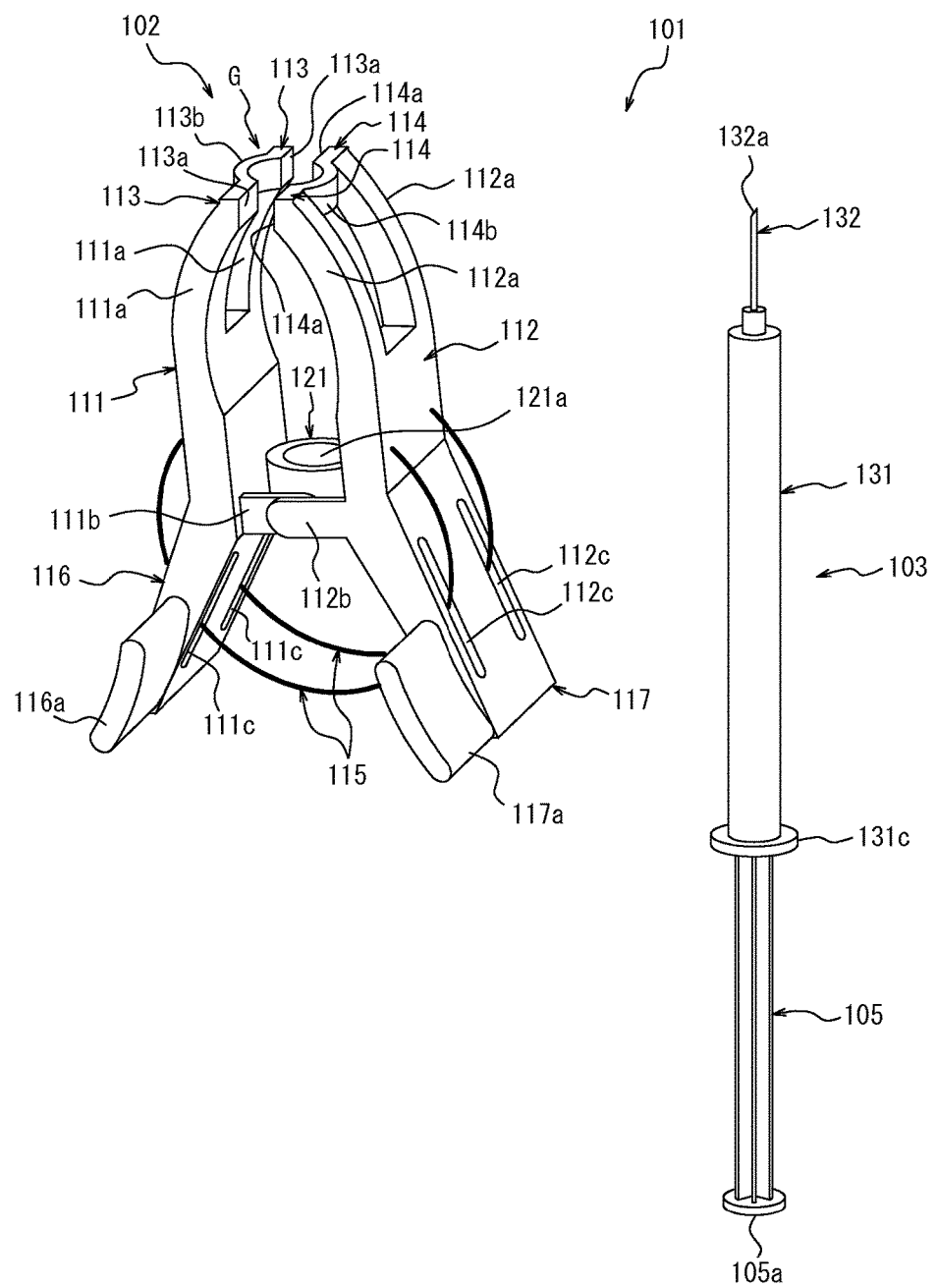
FIG. 9 is a perspective view of a puncture assisting device and a syringe that are included in a puncture device set according to a second embodiment of the invention.

A puncture device set 101 or a puncture assisting device 102 according to the second embodiment of the present invention, which is illustrated in FIG. 9, is used when a drug such as biological products is subcutaneously injected into a skin of an elbow joint stretching portion at an elbow in various treatments for rheumatoid arthritis or multiple sclerosis, for example. The puncture device set 101 includes the puncture assisting device 102 and a syringe 103. As the syringe used for the subcutaneous injection, a general syringe which is commercially available can also be used for the independent puncture assisting device 102.

The puncture assisting device 102 includes a first pinching piece 111 and a second pinching piece 112.

For example, the first pinching piece 111 and the second pinching piece 112 can be made of a synthetic resin such as an acrylic resin or an ABS resin, but can also be formed of other materials such as metal made of stainless steel and an aluminum alloy.

A pair of leg portions 111a are disposed on a distal side (upper side in FIG. 9) of the first pinching piece 111. These leg portions 111a respectively have a shape of being curved outward so as to widen a gap with the second pinching piece 112, and are arranged parallel to each other by leaving a gap therebetween. Similarly, a pair of leg portions 112a are disposed on a distal side (upper side in FIG. 9) of the second pinching piece 112. These leg portions 112a respectively have a shape of being curved outward so as to widen a gap with the first pinching piece 111, and are arranged parallel to each other by leaving a gap therebetween.

The first pinching piece 111 and the second pinching piece 112 have a substantially symmetrical shape, and are attached to each other in an arrangement in which outer shapes thereof are substantially aligned with each other.

A pair of hinge pieces 111b protruding inward are integrally disposed in the intermediate portion in the longitudinal direction of the inner side surface (surface facing the second pinching piece 112 side) of the first pinching piece 111. A pair of hinge pieces 112b protruding inward are integrally disposed in the intermediate portion in the longitudinal direction of the inner side surface (surface facing the first pinching piece 111 side) of the second pinching piece 112. The pair of hinge pieces 111b of the first pinching piece 111 are arranged by overlapping each other on the inside of the pair of respectively corresponding hinge pieces 112b of the second pinching piece 112, and are connected so as to be pivotable relative to the hinge pieces 112b by a pin portion (not illustrated). That is, the first pinching piece 111 can pivot relative to the second pinching piece 112 around the center of a pin portion of the hinge pieces 111b and 112b.

Without being limited to a configuration in which both of these are attached to each other so as to be relatively pivotable by the above-described hinge pieces 111b and 112b, the first pinching piece 111 and the second pinching piece 112 can also adopt a configuration in which both of these are attached to each other so as to be relatively pivotable by using other pivoting mechanisms.

First pinching portions 113 are respectively disposed in each distal end of the pair of leg portions 111a of the first pinching piece 111. Second pinching portions 114 are respectively disposed in each distal end of the pair of leg portions 112a of the second pinching piece 112. One of the first pinching portions 113 is arranged facing one of the second pinching portions 114 so that a flat pinching surface 113a thereof faces a flat pinching surface 114a of the second pinching portions 114. Similarly, one of the first pinching portions 113 is arranged facing the other of the second pinching portions 114 so that the flat pinching surface 113a thereof faces the flat pinching surface 114a of the second pinching portions 114.

Without being limited to the above-described arrangement, for example, the pair of first pinching portions 113 and the pair of second pinching portions 114 can also adopt a configuration in which the first pinching portions 113 and the second pinching portions 114 arranged so as to obliquely face each other are formed in a point-symmetrical shape around the central position of the four pinching portions 113 and 114. In this case, the pinching surface 113a of the first pinching portion 113 and the pinching surface 114a of the second pinching portion 114 which are arranged so as to obliquely face each other are parallel to and face each other. The pinching surfaces 113a and 114a of the other two pinching portions 113 and 114 which are arranged so as to obliquely face each other are parallel to and face each other. According to this configuration, any one of the four pinching surfaces 113a and 114a of the respective pinching portions 113 and 114 faces the central position of the four pinching portions 113 and 114. In this manner, it is possible to more stably pinch the skin S.

In addition, the number of the pinching portions 113 and 114 may be at least three. Four or more pinching portions can also be disposed. It is preferable that all of the pinching portions are arranged parallel to each other in an annular shape around the central position, regardless of the number of the pinching portions.

The pair of pinching portions 113 and the pair of pinching portions 114 can be opened and closed so as to move close to or away from each other by relatively pivoting the first pinching piece 111 and the second pinching piece 112. Then, the first pinching portion 113 and the second pinching portion 114 which are opened and closed can pinch the skin S by being closed in a state where the skin S of the elbow joint stretching portion at the elbow is pinched therebetween. In addition, the skin S pinched therebetween can be released by opening the first pinching portion 113 and the second pinching portion 114. The first pinching portion 113 and the second pinching portion 114 which are attached to each other so as to be openable and closeable in this way configure the skin collecting portion G for collecting and pinching the skin S.

The pair of pinching portions 113 disposed in the first pinching piece 111 are connected to each other by an arc-shaped first arc portion 113b which is integrally disposed therebetween. Similarly, the pair of pinching portions 114 disposed in the second pinching piece 112 are connected to each other by an arc-shaped second arc portion 114b which is integrally disposed therebetween. These arc portions 113b and 114b are curved in a direction where both of these respectively widen a gap therebetween.

As the biasing portion, a pair of C-springs 115 are mounted on the puncture assisting device 102. A pair of slit-like through-holes 111c for spring insertion are disposed in the first pinching piece 111. Similarly, a pair of slit-like through-holes 112c for spring insertion are disposed in the second pinching piece 112. The pair of C-springs 115 respectively have a shape in which a wire rod made of spring steel or stainless steel is curved in a C-shape, are respectively inserted into the corresponding through-holes 111c and 112c. One end thereof is supported by the outer side surface of the first pinching piece 111, and the other end thereof is supported by the outer side surface of the second pinching piece 112. In this manner, the first pinching portion 113 and the second pinching portion 114 are biased by the pair of C-springs 115 to be in a closed position, that is, in a direction of moving close to each other.

As the C-spring 115, it is also possible to use a resin-made spring or the like without being limited to the above-described spring steel or stainless steel. In addition, the biasing portion is not limited to the C-spring 115 having the above-described configuration. For example, other configurations using a helical spring, a torsion spring, and an elastic material such as rubber can also be adopted as long as the first pinching portion 113 and the second pinching portion 114 can be biased to be in the closed position.

A portion of the first pinching piece 111 which is located on the proximal side (opposite side to the side having the first pinching portion 113) further from the hinge piece 112b is a first gripping portion 116. A portion of the second pinching piece 112 which is located on the proximal side (opposite side to the side having the second pinching portion 114) further from the hinge piece 112b is a second gripping portion 117. In a state where the first pinching portion 113 and the second pinching portion 114 are closed, the first gripping portion 116 and the second gripping portion 117 face each other by leaving a gap therebetween. For example, these gripping portions 116 and 117 are pinched and pinched by two fingers, and are operated in the direction of moving close to each other. In this manner, the pair of pinching portions 113 and 114 can be opened by relatively pivoting the first pinching piece 111 and the second pinching piece 112. If the operation of the gripping portions 116 and 117 is halted, a spring force of the C-spring 115 causes the pair of pinching portions 113 and 114 to return to a closed state. That is, the pair of pinching portions 113 and 114 can be opened and closed by operating these gripping portions 116 and 117.

The gripping portions 116 and 117 can adopt a configuration in which finger hook portions 116a and 117a are integrally disposed parallel to a side of the gripping portions 116 and 117. In the illustrated case, the finger hook portions 116a and 117a are formed in a plate-like shape in which both of these are slightly warped so as to respectively project inward. These finger hook portions 116a and 117a are integrally disposed in the gripping portions 116 and 117. In this manner, fingers are likely to be hooked into the gripping portions 116 and 117. Accordingly, it is possible to improve operability thereof.

According to the configuration of the puncture assisting device 102 having a clip shape in this way, the gripping portions 116 and 117 are pinched and pinched by fingers so as to open the pair of pinching portions 113 and 114. In this state, the pair of pinching portions 113 and 114 are pushed against the skin S of the elbow joint stretching portion at the elbow in the vertical direction. Next, the operation of the gripping portions 116 and 117 is restarted. In this manner, the skin S can be pinched and held between the pair of pinching portions 113 and 114.

A syringe insertion portion 121 is disposed between the first pinching portions 113 and 114 and the gripping portions 116 and 117. In the illustrated case, the syringe insertion portion 121 is arranged inside the hinge pieces 111b and 112b, and is fixed to either the inner surface of the first pinching piece 111 or the inner side surface of the second pinching piece 112.

The syringe insertion portion 121 is formed in a cylindrical shape including an insertion hole 121a in the axial center, and the syringe 103 can be inserted into the insertion hole 121a. In addition, the syringe insertion portion 121 can hold the syringe 103 inserted into the insertion hole 121a.

The syringe insertion portion 121 is disposed by adopting a posture in which the insertion hole 121a is open toward the central position of the four pinching portions 113 and 114, that is, by adopting a posture in which the axial center of the insertion hole 121a passes through the central position of the four pinching portions 113 and 114. Therefore, the syringe 103 inserted into the insertion hole 121a of the syringe insertion portion 121 adopts a posture in which a needle 132 thereof faces the central position of the four pinching portions 113 and 114, that is, a posture in a direction along the central axis of the four pinching portions 113 and 114.

The central position of the four pinching portions 113 and 114 is the skin collecting portion G. However, in particular, it is most preferable to insert the needle 132 into a central position of a rectangle obtained by linearly connecting each reference position of the four pinching portions 113 and 114 (for example, a center position of the pinching portions 113a and 114a).

In the syringe insertion portion 121, a distal portion of the insertion hole 121a may be obliquely disposed so that the insertion hole 121a faces the central position in a state where the gripping portion 116 is opened. In addition, the syringe insertion portion 121 can also adopt a configuration in which the syringe insertion portion 121 is disposed integrally with the first pinching piece 111 or the second pinching piece 112. Furthermore, the syringe insertion portion 121 can also adopt a configuration in which a pin portion of the hinge penetrates the hinge pieces 111b and 112b and the syringe insertion portion 121, and in which the syringe insertion portion 121 always faces the central position in both states such as a state where the gripping portions 116 and 117 are opened and a state where the gripping portions 116 and 117 are closed. In this case, in order to prohibit the syringe insertion portion 121 from rotating around the pin portion of the hinge when the syringe is inserted or when the drug solution is injected, a configuration can also be adopted in which at least two pinching piece and elastic piece in the four pinching portions 113 and 114 hold the syringe insertion portion 121 in a posture of facing the central position.

As illustrated in FIG. 9, the syringe 103 includes a plunger 105, an outer cylinder body 131, and the needle 132.

The outer diameter of a portion close to the needle 132 of the outer cylinder body 131 of the syringe 103 is slightly smaller than the inner diameter of the insertion hole 121a of the syringe insertion portion 121. Therefore, the syringe 103 can be inserted into the insertion hole 121a of the syringe insertion portion 121. A configuration can also be adopted in which a stopper or the like is disposed in the outer cylinder body 131 of the syringe 103 so as to regulate an insertion depth of the syringe insertion portion 121 of the syringe 103 inserted into the insertion hole 121a, that is, a puncture depth of the needle 132 of the syringe 103 puncturing the skin S.

An annular finger hook flange 131c extending outward in the radial direction is integrally disposed in the opening end of the outer cylinder body 131. On the other hand, a disk-shaped thrusting flange 105a is integrally disposed in the proximal end of the plunger 105. In this manner, a forefinger and a middle finger are hooked into the finger hook flange 131c of the outer cylinder body 131, and a thumb is hooked into the thrusting flange 105a of the plunger 105. The thumb pushes the plunger 105 toward the inside of the outer cylinder body 131. In this manner, it is possible to easily perform an operation for dispensing a drug accommodated inside the outer cylinder body 131 outward from the needle tip 132a of the needle 132.

Next, referring to FIGS. 10 to 14, a procedure will be described in a drug administration method (drug solution injection method) in which a drug is subcutaneously injected into the skin S of an elbow joint stretching portion at an elbow by using the puncture device set 101 according to the second embodiment of the present invention.

Figure 10A:
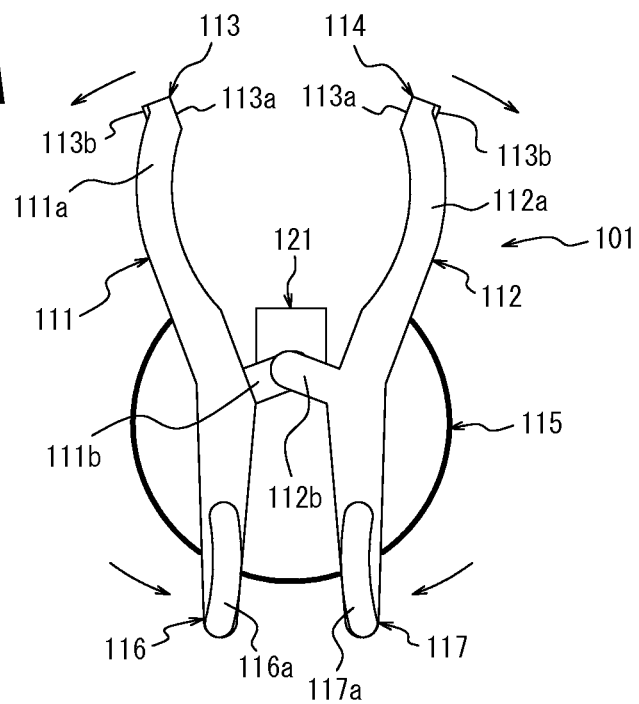
FIGS. 10A and 10B are views illustrating a procedure in which the puncture assisting device illustrated in FIG. 9 nips a skin of an elbow joint stretching portion at an elbow.

First, a skin pinching process of pinching the skin S of the elbow joint stretching portion at the elbow is performed by using the pair of pinching portions 113 and 114 of the puncture assisting device 102, that is, the skin collecting portion G. As illustrated in FIG. 10A, in the skin pinching process, a pair of gripping portions 116 and 117 and the finger hook portions 116a and 117a are pinched and pinched by fingers, for example, so as to open the pair of pinching portions 113 and 114.

Figure 10B:
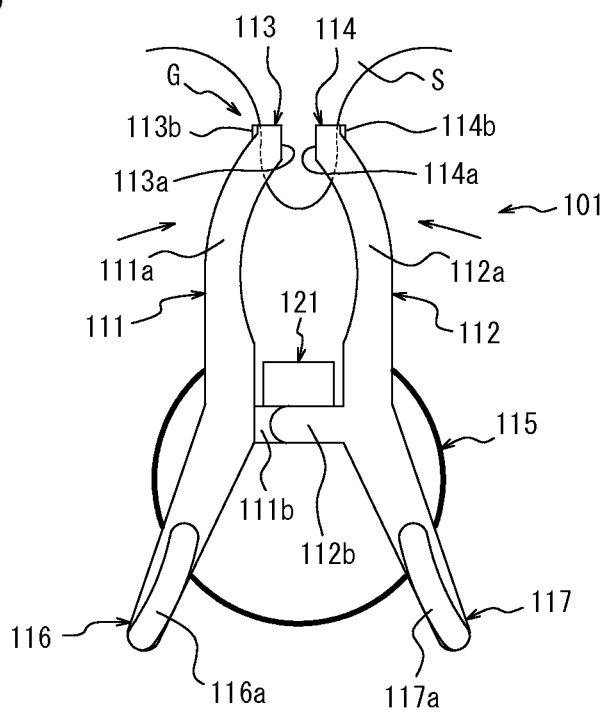

Next, in this state, the pair of pinching portions 113 and 114 are pushed against the skin S of the elbow joint stretching portion at the elbow in the vertical direction so as to release an operation force applied to the gripping portions 116 and 117 and the finger hook portions 116a and 117a. As illustrated in FIG. 10B, the skin S is pinched and held between the pinching portions 113 and 114. A spring force is applied to the pair of pinching portions 113 and 114 from the C-spring 115 in a closing direction thereof. Accordingly, the skin S pinched by the pinching portions 113 and 114 is brought into a state of being pressurized between the pinching portions 113 and 114.

Figure 11A:
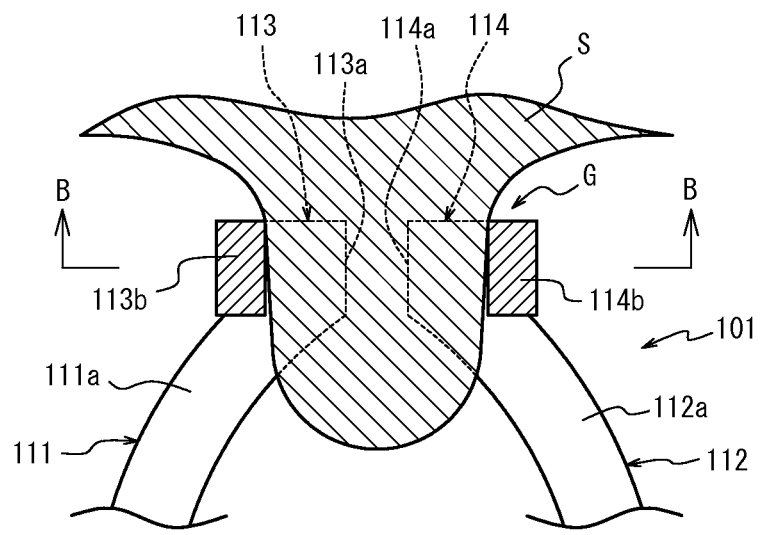
FIG. 11A is a sectional view illustrating in detail a state of the skin of the elbow joint stretching portion at the elbow which is pinched by pinching portions.
Figure 11B:
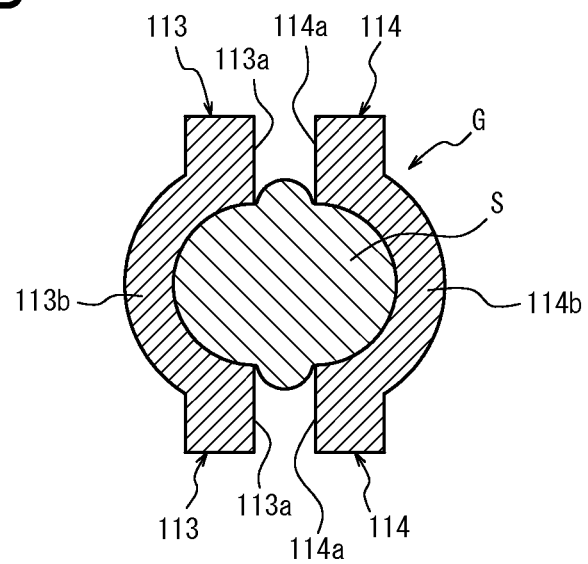
FIG. 11B is a sectional view taken along line B-B in FIG. 11A.

At this time, as illustrated in FIGS. 11A and 11B, the skin S is pinched in four directions by the four pinching portions 113 and 114. Accordingly, the skin S in the pinched portion has a substantially columnar shape. In addition, the pair of first pinching portions 113 are connected to each other by the first arch portion 113b, and the pair of second pinching portions 114 are connected to each other by the second arch portion 114b. Accordingly, a portion of the skin S pinched by the four pinching portions 113 and 114 is pinched between the arch portions 113b and 114b. In this manner, the skin S can be more reliably pinched in a columnar shape. In this way, the skin S pinched by the puncture assisting device 102 in the skin pinching process protrudes from the surface of the elbow in the columnar shape in the vertical direction.

In order to pinch the skin S as much as possible between the pair of pinching portions 113 and 114, before the skin pinching process, a collecting process can also be performed in which the skin S of the elbow joint stretching portion at the elbow is collected so that the skin S has a shape which is more likely to be pinched. For example, through the same work as that in the skin pinching process, the collecting process can be performed by using a method of pinching the skin S in a wider range, after the skin S is pinched between the pair of pinching portions 113 and 114, the skin S is once detached therefrom, and the pinching portions 113 and 114 are reopened. In this case, a configuration can also be adopted in which the skin S is more likely to be collected by disposing an adhesive material or an uneven shape, for example, in each distal portion of the pair of pinching portions 113 and the pair of pinching portions 114.

Without being limited to the above-described method, the collecting process can be performed by using a method in which the skin S is collected by a hand without using the puncture assisting device 102, or in which the skin S is collected by using other devices.

Figure 12A:
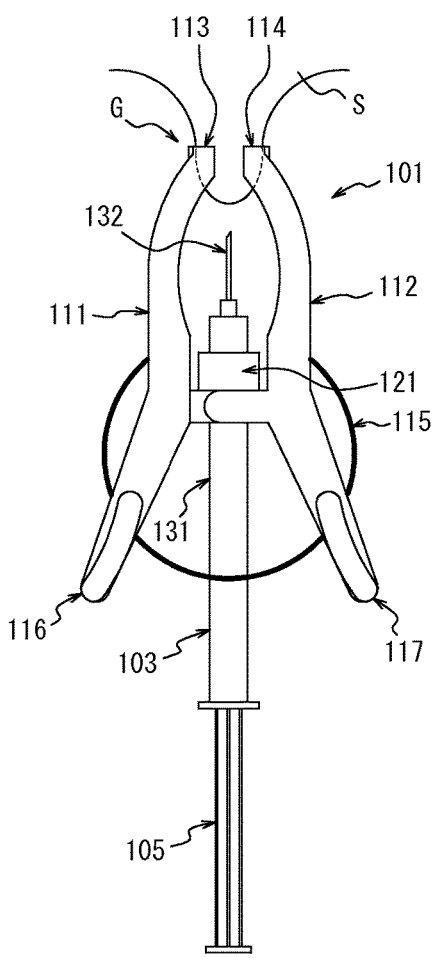
FIGS. 12A and 12B are views illustrating a procedure in which a needle of a syringe punctures the skin pinched by the puncture assisting device.

If the skin S is pinched by the puncture assisting device 102, next, as a syringe setting process, the syringe 103 is inserted into the insertion hole 121a of the syringe insertion portion 121. As illustrated in FIG. 12A, in the syringe setting process, the syringe 103 is inserted into the insertion hole 121a of the syringe insertion portion 121 in the vertical direction to the skin S of the elbow joint stretching portion at the elbow from a side having the gripping portions 116 and 117 of the puncture assisting device 102. In this manner, the syringe 103 is set in the syringe insertion portion 121.

Figure 12B:
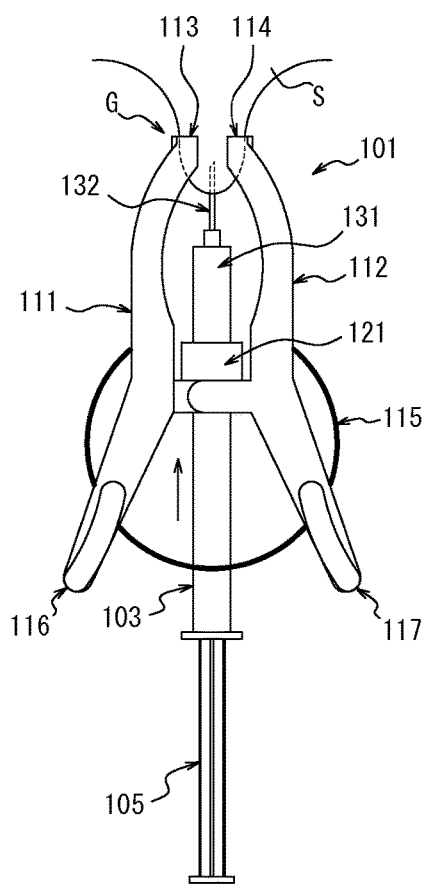

Next, as illustrated in FIG. 12B, as a puncture process, the syringe 103 set in the syringe insertion portion 121 is pushed toward a portion among the four pinching portions 113 and 114 along the syringe insertion portion 121, that is, toward the skin S pinched by the pinching portions 113 and 114 so that the needle 132 punctures the skin S in the vertical direction to the skin S pinched in the columnar shape at the central position of the four pinching portions 113 and 114. In this way, the needle 132 of the syringe 103 punctures the skin S along the central axis passing through the central position of the four pinching portions 113 and 114. Since the needle 132 vertically punctures the skin S, the number of nerves through which the needle 132 passes is reduced. Accordingly, it is possible to relieve pain caused by the puncture.

Each space is disposed between the respective leg portions 111a and 112a of the pinching pieces 111 and 112. In addition, the respective leg portions 111a and 112a have a curved shape so as to widen a gap therebetween. Accordingly, when the needle 132 of the syringe 103 punctures the skin S, it is possible to satisfactorily view and recognize progress of the puncture through a portion between the respective leg portions 111a and 112a. In this manner, it is possible to easily carry out puncture work of the needle 132 by using the puncture assisting device 102.

In a case of adopting a configuration in which a stopper or the like is disposed in the outer cylinder body 131 of the syringe 103 so as to regulate an insertion depth of the syringe 103 inserted into the insertion hole 121a of the syringe insertion portion 121, it is possible to regulate a puncture depth of the needle 132 of the syringe 103 puncturing the skin S (puncture depth regulating process). Therefore, it is possible to prevent the needle 132 of the syringe 103 from excessively deeply puncturing the skin S.

Figure 13:
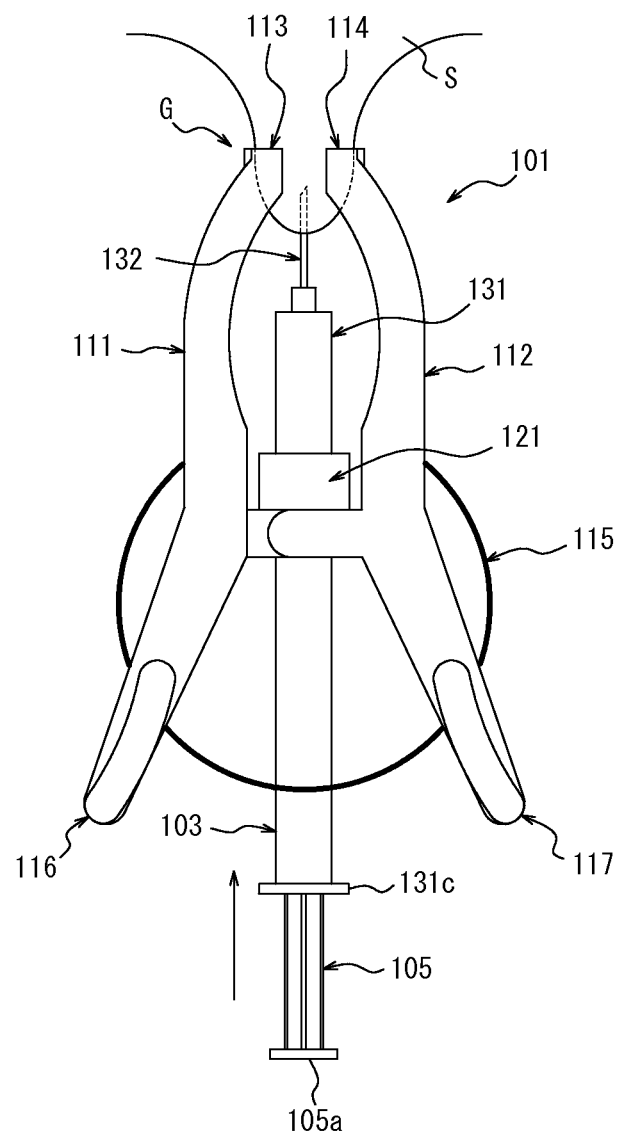
FIG. 13 is a view illustrating a state where a drug solution is injected into the skin by pushing a plunger of the syringe.

If the needle 132 of the syringe 103 punctures the skin S, next, as a drug injection process, as illustrated in FIG. 13, the plunger 105 of the syringe 103 is pushed toward the needle 132 side so as to inject the drug into the inside of the skin S through the needle 132 of the syringe 103. At this time, the skin S is pinched in a columnar shape by the puncture assisting device 102, and a space for the injected drug is likely to be subcutaneously formed. Accordingly, it is possible to relieve pain caused by invasive pressure when the drug is injected.

If the drug is completely injected in the inside of the skin S after the plunger 105 is pushed to reach a regulated position, the syringe 103 is pulled out from the syringe insertion portion 121 of the syringe 103 so as to perform a needle removal process of removing the needle 132 of the syringe 103 from the skin S.

Then, after the needle removal process, a pair of gripping portions 116 and 117 and the finger hook portions 116a and 117a are pinched and pinched by fingers, thereby performing a releasing process of releasing the force of the four pinching portions 113 and 114 pinching the skin S. In this manner, the skin S into which the drug is injected by the syringe 103 is released from a state of being pinched by the pinching portions 113 and 114 of the puncture assisting device 102. The releasing process may be performed before the needle removal process. In this case, during the releasing process or when the puncture assisting device 102 is moved away from the elbow joint stretching portion at the elbow, the needle 132 is naturally removed.

In this way, according to the above-described second embodiment of the present invention, the skin S of the elbow joint stretching portion at the elbow is stably pinched by the puncture assisting device 102, and the needle 132 of the syringe 103 punctures the skin S pinched by the puncture assisting device 102 in the vertical direction. In this manner, the drug can be administered into the skin S. Therefore, the puncture assisting device 102 is operated by using one hand so as to pinch the skin S of the elbow joint stretching portion at the elbow in the other arm. Subsequently, the syringe 103 held by using one hand detached from the puncture assisting device 102 is inserted into the insertion hole 121a of the syringe insertion portion 121. The needle 132 of the syringe 103 punctures the skin S pinched by the puncture assisting device 102 in the vertical direction. In this manner, the drug can be easily, safely, and subcutaneously injected into the skin S of the elbow joint stretching portion at the elbow by oneself.

In addition, it is possible to subcutaneously inject the drug into the skin S of the elbow joint stretching portion at the elbow by oneself. Accordingly, compared to a case where the drug is subcutaneously injected into other sites, a large amount of the drug can be administered without causing pain. In addition, a major nerve is not present in the skin S of the elbow joint stretching portion at the elbow. Accordingly, the needle 132 of the syringe 103 can safely puncture the skin S without giving damage to a nerve.

As illustrated in FIGS. 14A and 14B, in the drug administration method using the puncture assisting device 102 according to the present embodiment, as illustrated in FIG. 14A, first, a syringe setting process of setting the syringe 103 in the puncture assisting device 102 is performed. Thereafter, as illustrated in FIG. 14B, the skin S of the elbow joint stretching portion at the elbow is pinched by the four pinching portions 113 and 114, thereby enabling a configuration for performing a puncture process in which the needle 132 of the syringe 103 punctures the pinched skin S. In this case, the syringe 103 is set in advance at a predetermined position of the syringe insertion portion 121. Accordingly, the skin S pinched among the four pinching portions 113 and 114 gradually swells in a columnar shape, thereby allowing the needle 132 to automatically puncture the skin S in a process of being pinched among the four pinching portions 113 and 114. Therefore, the needle 132 of the syringe 103 can easily puncture the skin S through a simple operation, only by setting the syringe 103 in the syringe insertion portion 121 of the puncture assisting device 102 and causing the four pinching portions 113 and 114 to pinch the skin S in the vertical direction.

Even in this case, after the needle 132 of the syringe 103 punctures the skin S, the drug injection process, the releasing process, and the needle removal process are performed. However, the force of the four pinching portions 113 and 114 pinching the skin S is released by performing the releasing process, and the skin S is no longer held in the columnar shape. Accordingly, the needle removal process is performed as the skin S is automatically detached from the needle 132.

Figure 15:
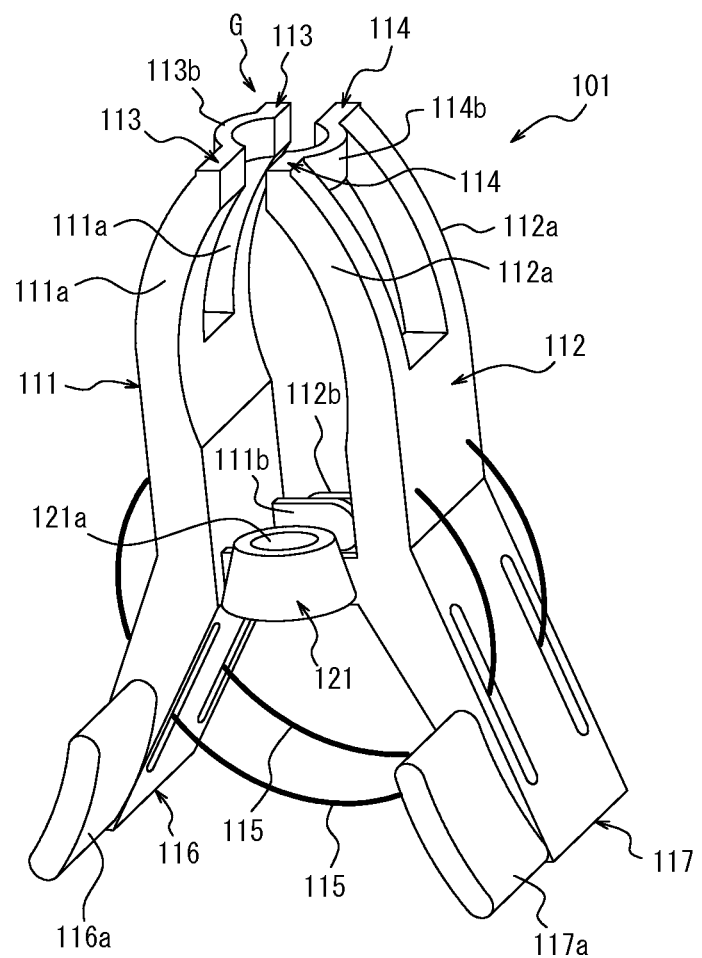
FIG. 15 is a perspective view illustrating a modification example of the puncture assisting device illustrated in FIG. 9.
Figure 16:
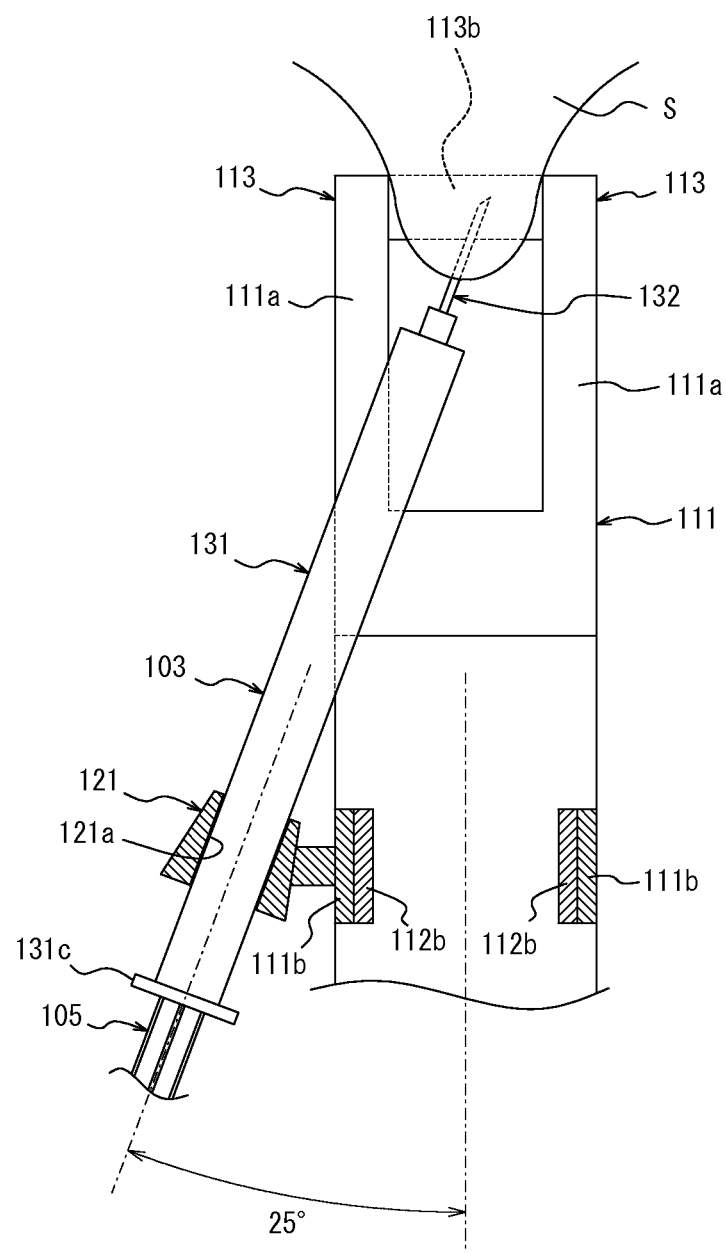
FIG. 16 is a view for describing an arrangement of a syringe insertion portion in the puncture assisting device illustrated in FIG. 15.

FIG. 15 is a perspective view illustrating a modification example of the puncture assisting device illustrated in FIG. 9. FIG. 16 is a view for describing an arrangement of a syringe insertion portion in the puncture assisting device illustrated in FIG. 15.

As illustrated in FIGS. 15 and 16, without being limited to a configuration in which the syringe insertion portion 121 is arranged inside the hinge pieces 111b and 112b, a configuration can also be adopted in which the syringe insertion portion 121 is arranged outside the hinge pieces 111b and 112b. Even in this case, the syringe insertion portion 121 is disposed by adopting a posture in which the insertion hole 121a is open toward the central position of the four pinching portions 113 and 114, that is, by adopting a posture in which the axial center of the insertion hole 121a passes through the central position of the four pinching portions 113 and 114. In the illustrated case, the syringe insertion portion 121 adopts a posture in which the axial direction of the insertion hole 121a is shifted as much as an angle of 25 degrees from an axial center L passing through the central position of the four pinching portions 113 and 114. In this case, it is preferable to pinch the skin S of the elbow joint stretching portion at the elbow by adopting a posture in which the first pinching portion 113 and the second pinching portion 114 are parallel to each other along the longitudinal direction of the stretched arm. In this manner, it is possible to easily carry out work for inserting the syringe 103 into the syringe insertion portion 121 in such a way that the insertion direction of the syringe 103 with respect to the puncture assisting device 102 is tilted toward the inner side of a body.

Figure 17A:
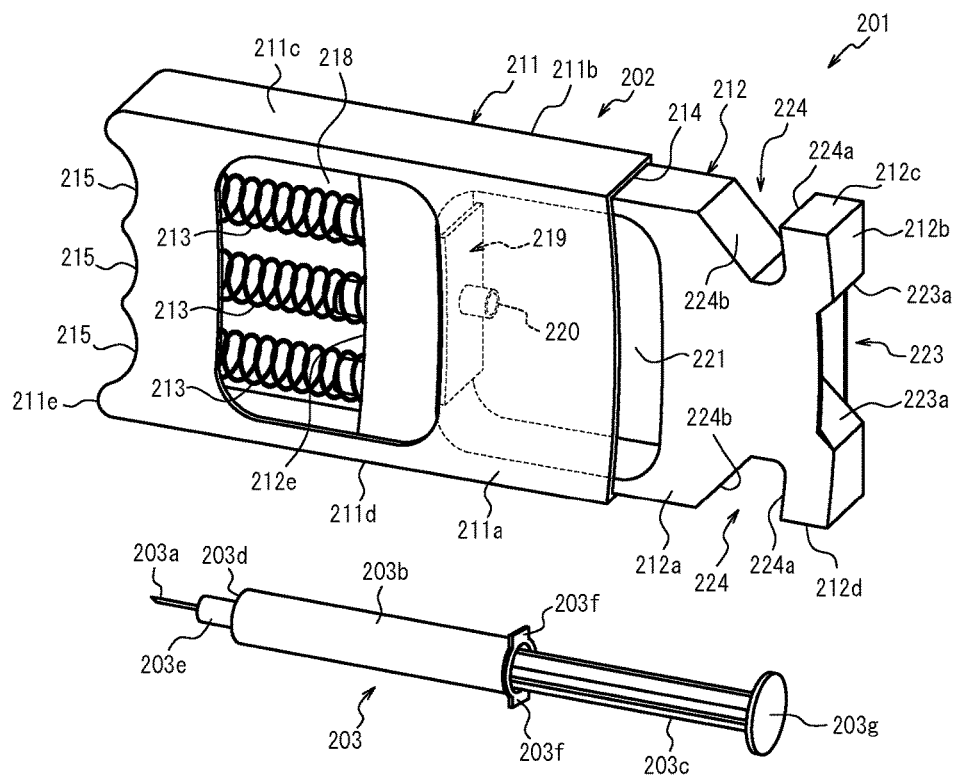
FIG. 17A is a perspective view of a puncture assisting device and a syringe which configure a puncture device set according to another embodiment of the invention.
Figure 17B:
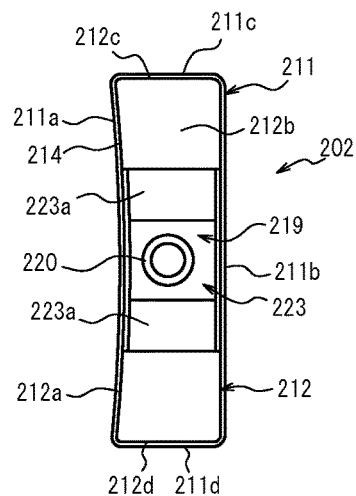
FIG. 17B is a side view of the puncture assisting device illustrated in FIG. 17A.
Figure 18A:
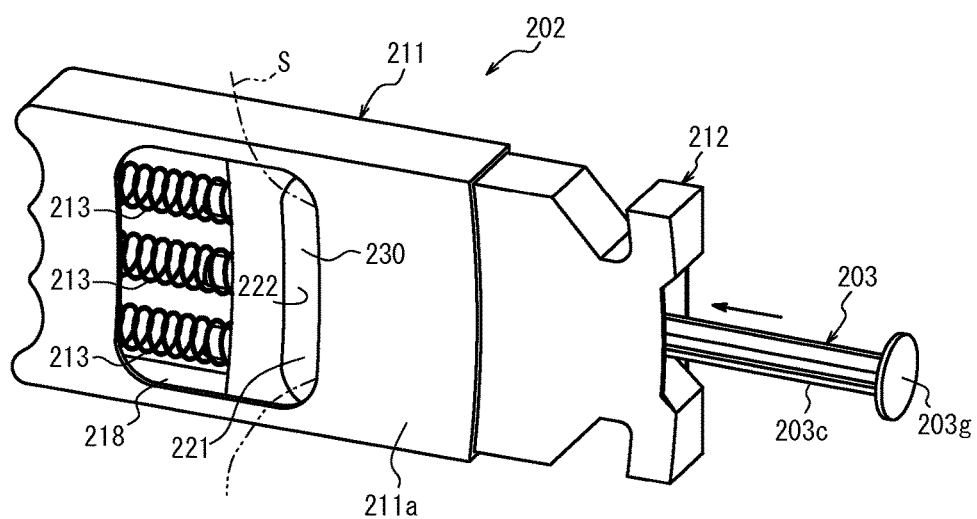
FIG. 18A is a perspective view illustrating a state where a needle of a syringe punctures a skin pinched by the puncture assisting device illustrated in FIGS. 17A and 17B.
Figure 18B:
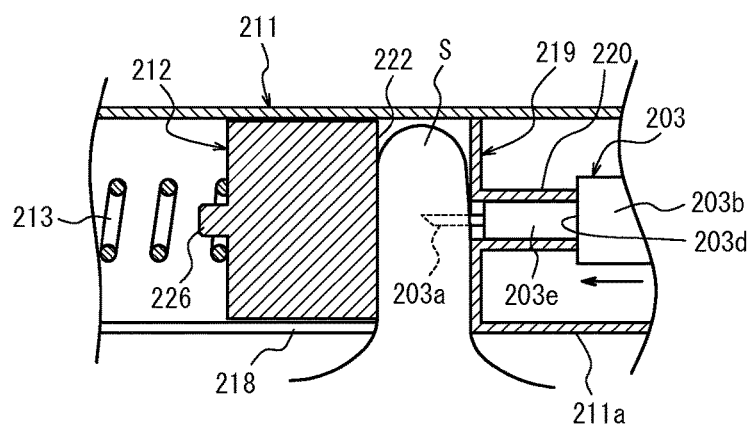
FIG. 18B is a sectional view thereof.

FIG. 17A is a perspective view of a puncture assisting device and a syringe that are included a puncture device set according to the other invention, and FIG. 17B is a side view of the puncture assisting device illustrated in FIG. 17A. In addition, FIG. 18A is a perspective view illustrating a state where a needle of a syringe punctures a skin pinched by the puncture assisting device illustrated in FIGS. 17A and 17B, and FIG. 18B is a sectional view thereof. Hereinafter, using a puncture device set 201 illustrated in FIGS. 17A and 17B will be described.

First, a space forming process of preparing a skin arrangement space 230 is performed in order to arrange the skin S of the elbow joint stretching portion at the elbow in a puncture assisting device 202. In the space forming process, a thumb is hooked into an end surface 212b of an inner gripping body 212, and the thumb pushes the inner gripping body 212 toward the inside of an outer gripping body 211. A forefinger, a middle finger, and a ring finger are hooked into a finger hooking concave portion 215 disposed on a blocking wall 211e of the outer gripping body 211. These fingers push the outer gripping body 211 toward the inner gripping body 212. In this manner, the inner gripping body 212 is moved against a spring 213 so as to reach an opening position with respect to the outer gripping body 211. Accordingly, it is possible to prepare the skin arrangement space 230 to be formed by a first opening portion 218 and a second opening portion 221 overlapping each other in the puncture assisting device 202.

In the space forming process, any finger may be hooked into the blocking wall 211e of the outer gripping body 211 and the end surface 212b of the inner gripping body 212. However, the thumb is hooked into the end surface 212b of the inner gripping body 212, and other fingers are hooked into the blocking wall 211e of the outer gripping body 211. In this manner, when the puncture assisting device 202 is caused to face the skin S of the elbow joint stretching portion at the elbow, the syringe insertion portion 223 can be directed to a front side of a body.

Next, in a state where an arm is stretched straight, a pushing process is performed by pushing the puncture assisting device 202 having the skin arrangement space 230 prepared therein against the skin S of the elbow joint stretching portion at the elbow. In the pushing process, the side wall 211a of the outer gripping body 211 of the puncture assisting device 202 is pushed against the skin S of the elbow joint stretching portion at the elbow. The skin S is arranged inside the first opening portion 218 and the second opening portion 221, that is, inside the skin arrangement space 230. At this time, the side wall 211a of the outer gripping body 211 is formed as a concave surface which is curved inward. Accordingly, the side wall 211a is fitted to the surface of the elbow joint stretching portion at the elbow. In this manner, the skin S of the elbow joint stretching portion at the elbow can be arranged inside the skin arrangement space 230 as much as possible.

Next, a skin pinching process is performed in order to pinch the skin S arranged in the skin arrangement space 230 between a first pinching portion 219 and a second pinching portion 222. In the skin pinching process, the side wall 211a of the outer gripping body 211 of the puncture assisting device 202 is pushed against the skin S of the elbow joint stretching portion at the elbow. In a state where the skin S is arranged in the skin arrangement space 230, the fingers are detached from the outer gripping body 211 and the inner gripping body 212. In this manner, the inner gripping body 212 is moved toward the closing position by the spring force of the spring 213. In this manner, the skin S arranged in the skin arrangement space 230 can be pinched between the first pinching portion 219 and the second pinching portion 222 which move in the direction of moving close to each other. At this time, the pinched skin S is caused to reach a portion having the needle insertion portion 220 of the first pinching portion 219. The spring force of the spring 213 is applied to the first pinching portion 219 and the second pinching portion 222 in the direction where both of these are closed. Accordingly, the skin S is held in a state of being pinched between the pinching portions 219 and 222.

The pinching portions 219 and 222 are respectively disposed in the outer gripping body 211 and the inner gripping body 212 which are attached to each other in this sliding manner, thereby adopting a configuration in which the skin S is pinched between the pinching portions 219 and 222. Accordingly, the skin S can be reliably pinched by performing a simple operation.

In order to enable the skin S to be reliably pinched as much as possible in the skin pinching process by arranging the skin S as much as possible inside the skin arrangement space 230, before the skin pinching process, a collecting process can also be performed in which the skin S of the elbow joint stretching portion at the elbow is collected so that the skin S has a shape which is more likely to be arranged inside the skin arrangement space 230 (shape which is more likely to be pinched). For example, through the same work as that in the skin pinching process, the collecting process can be performed by using a method of pinching the skin S in a wider range, after the skin S is pinched between the pair of pinching portions 219 and 222, the skin S is once detached therefrom, and the pinching portions 219 and 222 are reopened. In this case, a configuration can also be adopted in which the skin S is more likely to be collected by disposing an adhesive material or an uneven shape, for example, in each distal portion of the pair of pinching portions 219 and 222.

Without being limited to the above-described method, the collecting process can be performed by using a method in which the skin S is collected by a hand without using the puncture assisting device 202, or in which the skin S is collected by using other devices.

If the skin S is pinched between the pair of pinching portions 219 and 222 of the puncture assisting device 202, next, a puncture process is performed. In the puncture process, as illustrated in FIG. 18A, the syringe 203 is inserted through the syringe insertion portion 223 disposed in the inner gripping body 212. In the syringe 203, an outer peripheral surface of the outer cylinder body 203b comes into sliding contact with the inner surface of the syringe insertion portion 223, thereby causing the syringe insertion portion 223 to regulate the insertion direction of the syringe 203. At this time, the syringe insertion portion 223 is oriented to a front side of a body. In addition, the opening end of the syringe insertion portion 223 is formed in a tapered shape by a pair of slopes 223a. Accordingly, it is easy to carry out work for inserting the syringe 203 into the syringe insertion portion 223. If the syringe 203 is inserted into the syringe insertion portion 223, as illustrated in FIG. 18B, the needle 203a is inserted into the needle insertion portion 220. From a lateral side thereof, the needle 203a punctures the skin S of the elbow joint stretching portion at the elbow which is pinched between the first pinching portion 219 and the second pinching portion 222. In this way, a configuration is adopted in which the outer cylinder body 203b of the syringe 203 is guided to the syringe insertion portion 223, and in which a hub 203e is guided to the needle insertion portion 220. Accordingly, the needle 203a of the syringe 203 can easily and accurately puncture a predetermined site of the skin S by carrying out simple work for only inserting the syringe 203 into the syringe insertion portion 223.

In the puncture process, a needle support portion 203d of the syringe 203 comes into contact with the distal end of the needle insertion portion 220, thereby regulating the puncture depth to be a predetermined depth when the needle 203a of the syringe 203 punctures the skin S (puncture depth regulating process). Therefore, it is possible to prevent the needle 203a of the syringe 203 from excessively deeply puncturing the skin S or from penetrating the skin S.

If the needle 203a of the syringe 203 punctures the skin S, next, a drug injection process is performed. In the drug injection process, a plunger 203c of the syringe 203 is pushed toward the needle 203a side, thereby injecting a drug into the inside of the skin S through the needle 203a of the syringe 203. At this time, a forefinger and a middle finger are hooked into a constricting portion 224 disposed in both side surfaces 212c and 212d of the inner gripping body 212, and a thumb is hooked into the thrusting flange 203g of the plunger 203c. The thumb pushes the plunger 203c toward the inside of the outer cylinder body 203b. In this manner, it is possible to easily perform an operation for pushing the plunger 203c, that is, the drug injection process.

Then, a releasing process is performed in order to release the skin S of the elbow joint stretching portion at the elbow which is pinched between the first pinching portion 219 and the second pinching portion 222. In the releasing process, similarly to the space forming process, the thumb pushes the inner gripping body 212 and the other finger pushes the outer gripping body 211, thereby moving the inner gripping body 212 against the spring 213 so as to reach the opening position. In this manner, the first pinching portion 219 and the second pinching portion 222 are moved in the direction of moving away from each other. The first opening portion 218 and the second opening portion 221 are brought into an opened state, thereby releasing the skin S of the elbow joint stretching portion at the elbow which is pinched between the first pinching portion 219 and the second pinching portion 222. In addition, as the skin S is released, the needle 203a puncturing the skin S is removed from the skin S. Then, the skin S of the elbow joint stretching portion at the elbow is released from the puncture assisting device 202, thereby completing the drug administration.

After the plunger 203c is pushed to reach a regulated position and the drug is completely injected into the inside of the skin S, a needle removal process may be performed in order to remove the needle 203a of the syringe 203 from the skin S by pulling out the syringe 203 from the syringe insertion portion 223.

In this way, according to the present invention, the puncture assisting device 202 can more easily and stably pinch the skin S of the elbow joint stretching portion at the elbow. The needle 203a of the syringe 203 can easily and accurately puncture the skin S pinched between the pair of pinching portions 219 and 222 of the puncture assisting device 202 by carrying out simple work for only inserting the syringe 203 through the syringe insertion portion 223 disposed in the puncture assisting device 202. In this manner, the drug can be easily administered into the skin S. Therefore, the puncture assisting device 202 is operated by using one hand so as to pinch the skin S of the elbow joint stretching portion at the elbow in the other arm. Subsequently, the syringe 203 held by using one hand detached from the puncture assisting device 202 is inserted through the syringe insertion portion 223. Through this simple work, the needle 203a of the syringe 203 punctures the skin S pinched between the pair of pinching portions 219 and 222. In this manner, the drug can be easily, safely, and subcutaneously injected into the skin S of the elbow joint stretching portion at the elbow, using one hand by oneself.

Referring to FIGS. 17 and 18, the reference numeral 203f represents a flange of the syringe 203, the reference numerals 211b to 211d represent side walls of the outer gripping body 211, the reference numeral 212a represents a side surface of the inner gripping body 212, the reference numeral 212e represents a distal surface of the inner gripping body 212, the reference numeral 214 represents a combining opening of the outer gripping body 211, the reference numeral 224a represents a holding surface of the constricting portion 224, and the reference numeral 224b represents a slope of the constricting portion 224.

Without being limited to the above-described embodiments, the present invention can be modified in various ways within the scope not departing from the gist of the present invention, as a matter of course.

For example, in the present embodiment, a case has been described in which the puncture device sets 1, 101, and 201 are used in subcutaneously injecting the drug by pinching the skin S other than an elbow skin. However, it is also possible to use the puncture device sets 1 and 101 according to the present embodiment, when the drug is subcutaneously injected to other body sites.

REFERENCE SIGNS LIST

1 PUNCTURE DEVICE SET
2 PUNCTURE ASSISTING DEVICE
3 SYRINGE
4 PLUNGER SIDE ROD PORTION
4a TAPERED DISTAL PORTION
5 PLUNGER
5a THRUSTING FLANGE
11 FIRST PINCHING PIECE
11a CONCAVE PORTION
11b THROUGH-HOLE
11c LOCKING GROOVE
12 SECOND PINCHING PIECE
12a CONVEX PIECE PORTION
12b CONCAVE PORTION
12c THROUGH-HOLE
12d LOCKING GROOVE
13 FIRST PINCHING PORTION
13a GROOVE
14 SECOND PINCHING PORTION
14a GROOVE
15 PLATE SPRING (BIASING PORTION)
15a FIRST PLATE-LIKE PIECE
15b SECOND PLATE-LIKE PIECE
15c CURVED PIECE
15d LOCKING PORTION
16 FIRST GRIPPING PORTION
16a RIB
17 SECOND GRIPPING PORTION
17a RIB
18 HOLDING PIECE
18a HOLE
21 FIRST PUNCTURE GUIDE PORTION
21a GUIDE HOLE
22 SECOND PUNCTURE GUIDE PORTION
22a GUIDE HOLE
23 ROD INSERTION PORTION
24 SLOPE
31 OUTER CYLINDER BODY
31a NEEDLE SUPPORT PORTION
31b HUB
31c FINGER HOOK FLANGE
32 NEEDLE
32a NEEDLE TIP
33 ROD SUPPORT PORTION
101 PUNCTURE DEVICE SET
102 PUNCTURE ASSISTING DEVICE
103 SYRINGE
105 PLUNGER
105a THRUSTING FLANGE
111 FIRST PINCHING PIECE
111a LEG PORTION
111b HINGE PIECE
111c THROUGH-HOLE
112 SECOND PINCHING PIECE
112a LEG PORTION
112b HINGE PIECE
112c THROUGH-HOLE
113 FIRST PINCHING PORTION
113a PINCHING SURFACE
113b FIRST ARCH PORTION
114 SECOND PINCHING PORTION
114a PINCHING SURFACE
114b SECOND ARCH PORTION
115 C-SPRING
116 FIRST GRIPPING PORTION
116a FINGER HOOK PORTION
117 SECOND GRIPPING PORTION
117a FINGER HOOK PORTION
121 SYRINGE INSERTION PORTION
121a INSERTION HOLE
131 OUTER CYLINDER BODY
131c FINGER HOOK FLANGE
132 NEEDLE
132a NEEDLE TIP
201 PUNCTURE DEVICE SET
202 PUNCTURE ASSISTING DEVICE
203 SYRINGE
203a NEEDLE
203b OUTER CYLINDER BODY
203c PLUNGER
203d NEEDLE SUPPORT PORTION
203e HUB
203f LOCKING FLANGE
203g THRUSTING FLANGE

211 OUTER GRIPPING BODY
211a to 211d SIDE WALL
211e BLOCKING WALL
212 INNER GRIPPING BODY
212a,212c,212d SIDE SURFACE
212b END SURFACE
212e DISTAL SURFACE
213 SPRING
214 COMBINING OPENING
215 CONCAVE PORTION
218 FIRST OPENING PORTION
219 FIRST PINCHING PORTION
220 NEEDLE INSERTION PORTION
221 SECOND OPENING PORTION
222 SECOND PINCHING PORTION
223 SYRINGE INSERTION PORTION
223a SLOPE
224 CONSTRICTING PORTION
224a HOLDING SURFACE
224b SLOPE
230 SKIN ARRANGEMENT SPACE
S SKIN
G SKIN COLLECTING PORTION

What is claimed is:

1. A method of administering a drug to an individual, the method comprising:
providing a puncture assisting device comprising:
a plurality of pinching portions that face each other, and that are attached to each other so as to be openable and closeable;
a rod insertion portion that is disposed between the plurality of pinching portions;
a biasing portion that biases the plurality of pinching portions to be in a closed position;
a pair of gripping portions configured to operate the plurality of pinching portions to be in an open position;
providing a syringe comprising a needle, an outer cylinder body accommodating a drug, and a plunger that includes a rod portion;
gripping the gripping portions so as to operate the plurality of pinching portions to be the open position,
pinching skin of an elbow joint stretching portion of the individual with the pinching portions of the puncture assisting device;
puncturing said skin with the needle of the syringe; and
pushing the plunger of the syringe and thereby injecting the drug into the individual, wherein, when the plunger is pushed, the rod portion of the syringe is inserted into the rod insertion portion of the puncture assisting device, thereby widening a gap between the plurality of pinching portions.

2. The method of claim 1, wherein
the biasing portion comprises a U-shaped plate spring including a first plate-like piece supported by a first one of the pinching portions, a second plate-like piece supported by a second one of the pinching portions, and a curved piece connecting the first plate-like piece and the second plate-like piece to each other, and
wherein the rod insertion portion is disposed between the first plate-like piece and the second plate-like piece.

3. The method of claim 1, wherein the rod insertion portion has a portion whose sectional area gradually decreases toward an inner side from an entrance side, such that the gap between the plurality of pinching portions is gradually widened as the rod portion is inserted into the rod insertion portion.

4. The method of claim 1, wherein:
at least one of the pinching portions comprises a puncture guide portion located at a side of said at least one pinching portion, and
the method further comprises, before puncturing said skin with the needle of the syringe, inserting the needle of the syringe into the puncture guide portion.

5. The method of claim 4, wherein the puncture guide portion is formed in a ring shape including a guide hole.

6. The method of claim 5, wherein an axis of the guide hole is perpendicular to directions in which the pinching portions extend.

7. The method of claim 5, wherein:
the syringe comprises a needle support portion supporting the needle, and
the guide hole has a smaller diameter than an outer diameter of the needle support portion of the syringe.

8. The method of claim 1, wherein the rod insertion portion has a portion with a sectional area that is smaller than a sectional area of the rod portion.

9. The method of claim 1, wherein:
the plurality of pinching portions includes a first pair of pinching portions disposed in a first pinching piece, and a second pair of pinching portions disposed in a second pinching piece, and
the pinching portions of each of the first and second pair of pinching portions are connected to each other by an arc-shaped portion, such that, when said skin is pinched, the pinched skin takes a substantially columnar shape.

10. The method of claim 9, wherein the puncture assisting device further comprises a syringe insertion portion having an insertion hole, and an axis of the insertion hole is coaxial with an axis of an opening formed by the arc-shaped portions.

11. The method of claim 1, wherein the puncture assisting device further comprises a syringe insertion portion having an insertion hole.

* * * * *